(12) United States Patent
Gardeski et al.

(10) Patent No.: US 7,130,700 B2
(45) Date of Patent: Oct. 31, 2006

(54) MULTILUMEN BODY FOR AN IMPLANTABLE MEDICAL DEVICE

(75) Inventors: Kenneth C. Gardeski, Plymouth, MN (US); Michael R. Leners, East Bethel, MN (US)

(73) Assignee: Medtronic, Inc., Minneapolis, MN (US)

( * ) Notice: Subject to any disclaimer, the term of this patent is extended or adjusted under 35 U.S.C. 154(b) by 539 days.

(21) Appl. No.: 10/299,484

(22) Filed: Nov. 19, 2002

(65) Prior Publication Data
US 2004/0097965 A1    May 20, 2004

(51) Int. Cl.
*A61N 1/375* (2006.01)
*A61B 19/00* (2006.01)

(52) U.S. Cl. ............ 607/122; 607/116; 607/119; 607/123; 600/585; 604/43; 604/171

(58) Field of Classification Search ........ 607/122–123, 607/37, 116, 119; 600/407, 585; 174/113 C, 174/113 R, 115, 116; 604/43, 171, 524
See application file for complete search history.

(56) References Cited

U.S. PATENT DOCUMENTS

| | | | | | |
|---|---|---|---|---|---|
| 3,692,029 | A | * | 9/1972 | Adair ........................ 604/105 |
| 3,911,928 | A | * | 10/1975 | Lagergren ................. 607/122 |
| 4,106,512 | A | | 8/1978 | Bisping |
| 4,444,195 | A | * | 4/1984 | Gold ......................... 600/374 |
| 4,778,246 | A | * | 10/1988 | Carroll ...................... 385/107 |
| 4,819,662 | A | * | 4/1989 | Heil et al. ................. 607/116 |
| 4,915,490 | A | * | 4/1990 | Ramsay et al. ........... 385/100 |
| 5,005,587 | A | * | 4/1991 | Scott ......................... 607/122 |
| 5,016,646 | A | * | 5/1991 | Gotthardt et al. ......... 607/122 |
| 5,042,486 | A | | 8/1991 | Pfeiler et al. |
| 5,203,772 | A | * | 4/1993 | Hammerslag et al. ..... 604/528 |
| 5,217,028 | A | * | 6/1993 | Dutcher et al. ............ 607/120 |
| 5,228,441 | A | * | 7/1993 | Lundquist .................. 600/380 |
| 5,259,394 | A | * | 11/1993 | Bens ......................... 607/127 |
| 5,303,704 | A | * | 4/1994 | Molacek et al. ........... 600/377 |
| 5,330,520 | A | * | 7/1994 | Maddison et al. ......... 607/122 |
| 5,330,522 | A | * | 7/1994 | Kreyenhagen ............ 607/122 |
| 5,354,327 | A | * | 10/1994 | Smits ........................ 607/116 |
| 5,368,564 | A | * | 11/1994 | Savage .................... 604/95.04 |
| 5,496,360 | A | * | 3/1996 | Hoffmann et al. ......... 607/120 |
| 5,499,981 | A | * | 3/1996 | Kordis ...................... 606/41 |
| 5,500,012 | A | * | 3/1996 | Brucker et al. ............ 607/122 |
| 5,514,171 | A | * | 5/1996 | Hoegnelid et al. ........ 607/122 |
| 5,514,172 | A | * | 5/1996 | Mueller ..................... 607/122 |
| 5,531,781 | A | * | 7/1996 | Alferness et al. .......... 607/122 |

(Continued)

FOREIGN PATENT DOCUMENTS

DE    WO 03/008018    1/2003

*Primary Examiner*—Robert E. Pezzuto
*Assistant Examiner*—Deborah Malamud
(74) *Attorney, Agent, or Firm*—Michael C. Soldner; Girma Wolde-Michael

(57) ABSTRACT

A splined multilumen body for use in elongated medical devices is provided for carrying multiple conductors, wires or cables to multiple device components along the device body. Open lumens may be provided through which medical devices or therapies may be delivered. The multilumen body is constructed from a generally tubular outer member having inward-radiating splines that mate with outward-radiating splines on a generally tubular inner member. Lumens formed between sets of mated splines isolate conductors carried therein. Interaction of mated splines provides good torque transfer between outer and inner members. Materials for fabricating outer and inner members may be selected to achieve desired torque transfer properties, flexibility, and surface friction.

19 Claims, 19 Drawing Sheets

U.S. PATENT DOCUMENTS

| | | | |
|---|---|---|---|
| 5,545,200 A * | 8/1996 | West et al. | 607/122 |
| 5,584,873 A | 12/1996 | Shoberg et al. | |
| 5,592,939 A | 1/1997 | Martinelli | |
| 5,762,631 A | 6/1998 | Klein | |
| 5,796,044 A * | 8/1998 | Cobian et al. | 174/103 |
| 5,833,604 A * | 11/1998 | Houser et al. | 600/373 |
| 5,935,159 A * | 8/1999 | Cross et al. | 607/116 |
| 5,957,966 A * | 9/1999 | Schroeppel et al. | 607/122 |
| 5,968,082 A * | 10/1999 | Heil | 607/37 |
| 5,983,126 A | 11/1999 | Wittkampf | |
| 6,002,969 A * | 12/1999 | Machek et al. | 607/122 |
| 6,018,684 A * | 1/2000 | Bartig et al. | 607/122 |
| 6,083,170 A | 7/2000 | Ben-Haim | |
| 6,104,944 A | 8/2000 | Martinelli | |
| 6,181,971 B1 * | 1/2001 | Doan | 607/116 |
| 6,210,362 B1 | 4/2001 | Ponzi | |
| 6,249,708 B1 * | 6/2001 | Nelson et al. | 607/122 |
| 6,253,111 B1 * | 6/2001 | Carner | 607/122 |
| 6,253,770 B1 | 7/2001 | Acker et al. | |
| 6,287,326 B1 | 9/2001 | Pecor | |
| 6,323,459 B1 | 11/2001 | Maynard | |
| 6,445,958 B1 * | 9/2002 | Machek et al. | 607/122 |

* cited by examiner

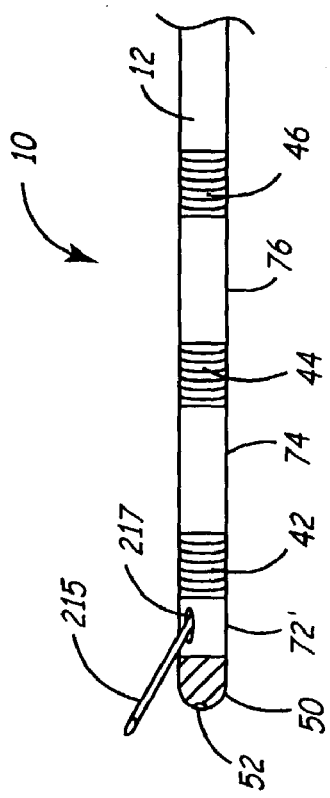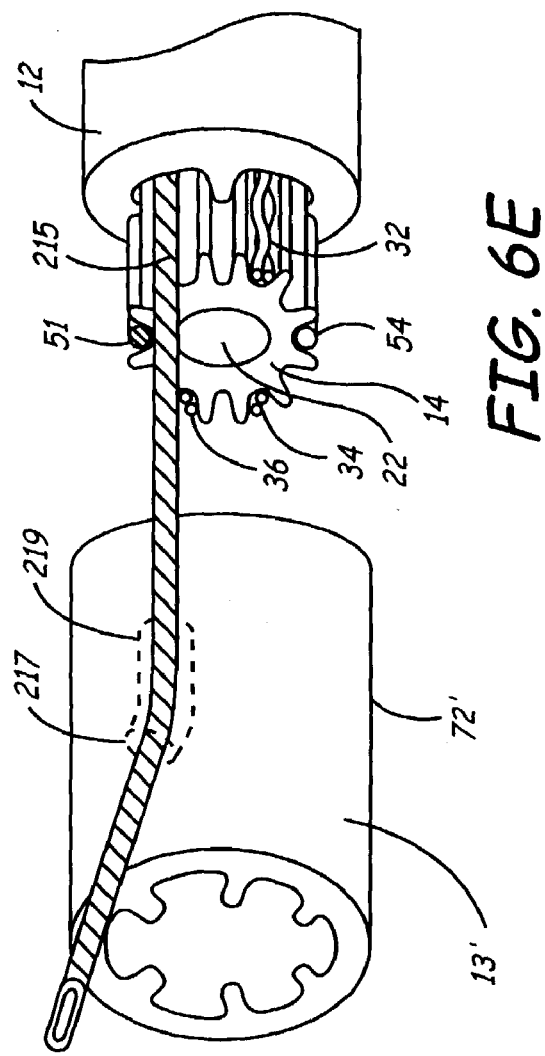

MULTILUMEN BODY FOR AN IMPLANTABLE MEDICAL DEVICE

CROSS-REFERENCE TO RELATED PATENT APPLICATIONS

The present invention is related to co-pending U.S. patent application Ser. No. 10/299,969 to Hunter et al., entitled "Navigation System for Cardiac Therapies".

FIELD OF THE INVENTION

The present invention relates generally to elongated medical devices such as catheters and leads, and more specifically, the present invention relates to a multilumen body for carrying multiple conductors included in an elongated medical device.

BACKGROUND OF THE INVENTION

Various specialized medical devices, such as cardiac leads, ablation catheters, electrophysiological diagnostic catheters, pressure monitoring catheters etc., require the use of a delivery system for deploying the device in a desired internal body space, such as the heart or vascular system. Delivery systems commonly include a steerable guide catheter. The guide catheter may be steered to a desired internal body location allowing a medical device to be deployed at a desired site through a central lumen of the catheter. Other types of medical therapies, such as genetic, biologic, or pharmacological agents, may require local administration through a delivery catheter. An implant or therapy delivery site generally needs to be carefully selected in order to achieve a desired therapeutic effect. Typically the location of a guide catheter within a patient's body is determined by taking a fluoroscopic image during the procedure. Multiple fluoroscopic images may be needed during a single procedure in order to follow the progress of a guide catheter as the guide catheter is advanced within the patient's body.

In order to avoid repeated exposure of the patient and operating room staff to ionizing fluoroscopic radiation, navigable guide catheters have been proposed that are equipped with location sensors for determining the location of a guide catheter within the patient's body. Locatable or navigable guide catheters are generally disclosed in U.S. Pat. No. 5,042,486 issued to Pfeiler et al., U.S. Pat. No. 5,592,939 issued to Martinelli, U.S. Pat. No. 6,253,770 issued to Acker et al., and U.S. Pat. No. 6,210,362 issued to Ponzi et al. One type of location sensor is an electromagnetic coil in which current is induced by an externally applied electromagnetic field. The location of the sensor coil relative to the external field source is determined from the measured current.

Image guided medical and surgical procedures utilize patient images obtained prior to or during a medical procedure to guide a physician performing the procedure. The location of a navigable catheter may be displayed on an image of the navigation domain taken prior to a procedure. An image guided catheter navigation system that enables the physician to see the location of a catheter relative to a patient's anatomy, without the need to acquire real-time fluoroscopic images is generally disclosed in co-pending U.S. patent application Ser. No. 10/299,969 to Hunter et al., entitled "Navigation System for Cardiac Therapies". In this system, it is desirable to locate and display a distal segment of the catheter rather than a single point such that navigation of the catheter is more intuitive to the physician. Therefore, it is desirable to include multiple location sensors along a segment of the navigable guide catheter. A system for navigating a catheter within a navigational domain including a catheter having locatable electrode elements distributed along and affixed to a length of the catheter is disclosed in U.S. Pat. No. 6,104,944 issued to Martinelli.

It may be further desirable to provide additional components along the catheter body such as stimulating or sensing electrodes or other types of physiological sensors to allow physiological signals to be monitored for diagnostic purposes or for selecting a therapy delivery site during advancement of the catheter. Thus it is desirable to provide a navigable guide catheter having multiple lumens for carrying multiple conductors between a proximal end of the catheter and multiple location sensors and any other optional sensors or electrodes that may be present in addition to providing an open lumen through which a medical device may be deployed or medical therapy may be administered.

Guide catheters are sometimes provided with reinforcing braiding within the wall of the catheter body. Such reinforcing braiding promotes kink resistance and can improve the amount of torque transferred between the proximal and distal end of the catheter. Efficient torque transfer is often desirable in catheter bodies to improve handling of the catheter as the catheter is steered along a desired pathway. A limitation of such braiding is that, when the braiding is formed from a metallic material, the braiding may interfere with the performance of electromagnetic location sensors by shielding the sensors from an externally applied electromagnetic field. However, the magnitude of the shielding effect is relative, and therefore some systems may work with braided shafts. Factors affecting the degree of shielding include the braid configuration, the receiver coil sensitivity and the source field strength. If the braid does extend over the receiver coil but is terminated before the coil, the braiding may not interfere with the location sensor function. However, it is desirable to provide a multilumen catheter body that provides good kink-resistance, variable stiffness, and efficient torque transfer without the incorporation of reinforcing braiding.

Multipolar medical leads may also employ a multilumen body for carrying multiple conductors between a proximal lead end and electrodes located along the lead body or at a distal end of the lead body. Cardiac leads having three, four, or more electrodes may be used for sensing cardiac signals and for delivering stimulation in the form of pacing, or cardioversion or defibrillation shock therapy. Multipolar leads may also be used for sensing and stimulating at multiple sites within the heart. Cardiac leads generally need to be highly flexible in order to withstand continuous flexing motion caused by the beating heart without fracturing. A stiff stylet advanced through a lumen of a lead body provides a flexible lead with the stiffness needed to advance the lead through a venous pathway. Leads may also be advanced over a guidewire, sometimes referred to as "over-the-wire" leads, however, a guide catheter is still often used during the placement of an "over-the-wire" lead for backup support and also because the flexible lead body may not have sufficient torque transfer from its proximal to distal end to allow the lead body to be rotated as the lead body is advanced through a venous pathway and fixed at a final location. Guide catheters, and particularly guide catheters having reinforcing braiding material within the catheter walls, provide effective torque transfer that may be needed for advancing and fixing a lead. However, during the implantation procedure the size of the guide catheter may limit the ability to advance a small diameter lead into narrow locations, such as within the cardiac veins. It is therefore desirable to provide a multilumen lead body having a desired degree of torque transfer from its proximal to distal end and the flexibility needed to withstand repeated flexion.

Multilumen lead bodies are generally formed as a multi-lumen extrusion. One multilumen lead body is described in U.S. Pat. No. 5,584,873 issued to Shoberg et al. In order to assemble a multipolar lead employing a single extruded multilumen body, each conductor for each electrode is threaded through a lumen of the lead body one at a time. As the number of electrodes and associated conductors increases, and as lead bodies are reduced in size to allow for easier implantation within a patient's vessels, the task of threading each conductor through its respective lumen can become tedious and time consuming. It is desirable, therefore, to provide a multilumen body that allows assembly of multiple conductors within the body to be performed quickly and easily.

What is needed therefore, is an improved multilumen elongated body for use with medical catheters or leads that is kink-resistant, allows for a desired degree of torque transfer from its proximal to distal end without reinforcing braiding material, and multiple conductors to be readily assembled within the multilumen body.

SUMMARY OF THE INVENTION

The present invention is directed to a multilumen body of an implantable medical device that includes a first tubular member, having a first plurality of members, and a second tubular member, having a second plurality of members. Pair of one of the first plurality of members and the second plurality of members form receiving portions receiving the other of the first plurality of members and the second plurality of members to fixedly engage the first tubular member and the second tubular member. The first tubular member and the second tubular member form a plurality of lumens extending from a proximal end through a distal end of the multibody lumen, the plurality of lumens receiving elongated members therein.

According to another preferred embodiment of the present invention, a multilumen body of an implantable medical device includes a first tubular member having a first plurality of members, and a second tubular member having a second plurality of members. Pairs of one of the first plurality of members and the second plurality of members form receiving portions receiving the other of the first plurality of members and the second plurality of members to fixedly engage the first tubular member and the second tubular member. A wall portion extends between adjacent members of the other of the first plurality of members and the second plurality of member, and a plurality of lumens that receive elongated members therein extend from the proximal end through the distal end of the multibody lumen are formed by the wall portion and adjacent pairs of the one of the first plurality of members and the second plurality of members forming the receiving portion.

The elongated members preferably include one or more of a conductor, a fluid delivery needle, and a deflection member, the deflection member transferring tension applied along the proximal end of the multilumen body to advance the distal end of the multilumen body between a non-deflected position and a deflected position As a result, torque applied along the proximal end of the multilumen body is transferred to the distal end of the multilumen body through the first tubular member and the second tubular member.

According to yet another preferred embodiment of the present invention, the first tubular member is formed of a first material and the second tubular member is formed of a second material different from the first material.

In accordance with another preferred embodiment of the present invention, a plurality of sensors are axially spaced along the distal end of the multilumen body, and the elongated members include conductors coupled to the plurality of sensors. An anchoring member is positioned along the distal end of the multilumen body, and the elongated members include a deflection member, coupled to the anchoring member, transferring tension applied along the proximal end of the multilumen body to advance the distal end of the multilumen body between a nondeflected position and a deflected position.

In still yet another preferred embodiment of the present invention, a plurality of electrodes are axially spaced along the distal end of the multilumen body, and the elongated members include conductors coupled to the plurality of electrodes. A plurality of anchoring members are positioned along a plurality of longitudinal locations along the distal end of the multilumen body, and the elongated members further include a plurality of deflection members coupled to the plurality of anchoring members, the plurality of deflection members transferring tension applied along the proximal end of the multilumen body to advance the distal end of the multilumen body between a non-deflected position and a deflected position.

BRIEF DESCRIPTION OF THE DRAWINGS

FIG. 6C is a plan view of the distal end of a navigable catheter having a multilumen body including a fluid delivery needle that may additionally serve as an anchoring mechanism.

FIG. 6E is a partially exploded, perspective view of the distal end of the multilumen body of FIG. 6C.

DETAILED DESCRIPTION OF THE INVENTION

Figure 1:
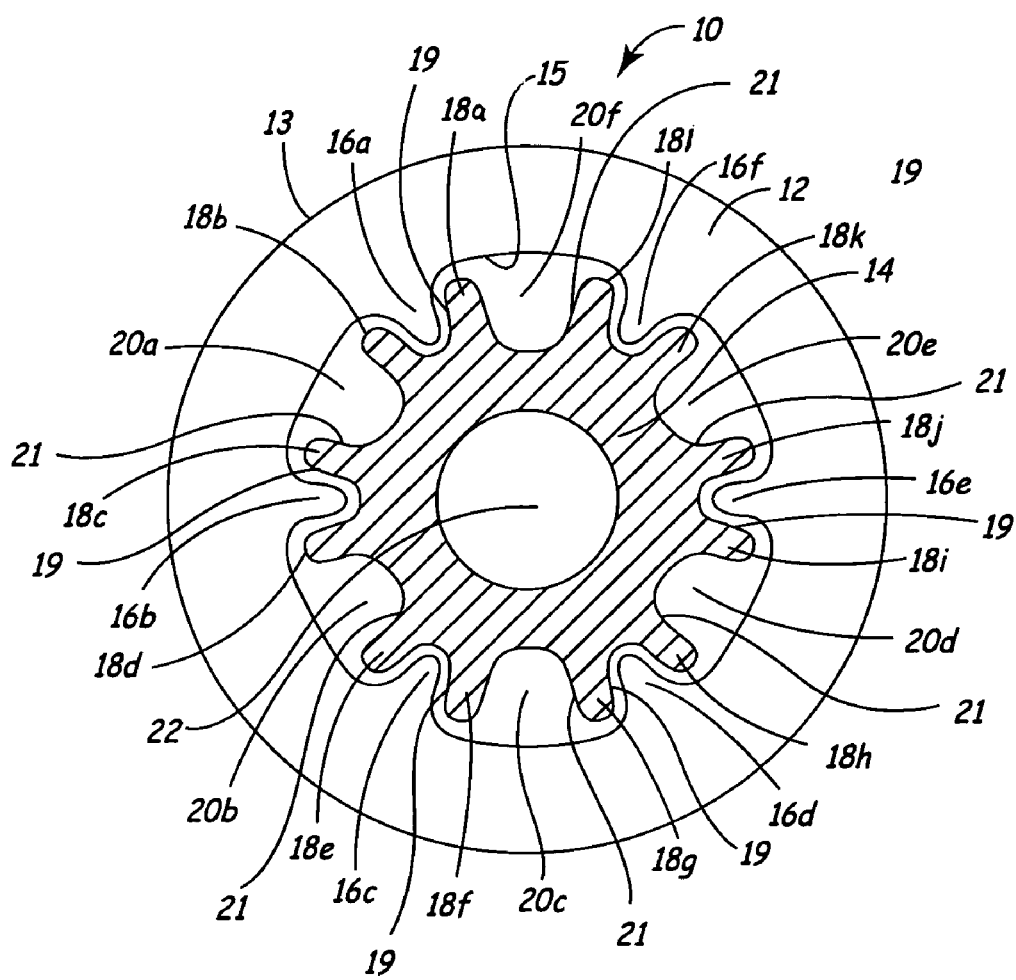
FIG. 1 is a cross-sectional view of a multilumen body according to the present invention.

As indicated above, the present invention relates to an improved multilumen body for use in elongated medical devices, such as catheters or leads, that require multiple lumens for carrying multiple conductors, wires, or cables or through which a medical device may be deployed or a medical therapy may be administered.

The present invention addresses the above described needs by providing a multilumen body for use in medical devices with properties that allow for a desired degree of torque transfer, excellent kink resistance and improved assembly methods. The present invention is realized by providing an elongated medical device body having a generally tubular, splined inner insulating member mated with a generally tubular, splined outer insulating member. The outer insulating member is provided with multiple inward-radiating splines on its inner diameter that extend longitudinally the length of outer insulating member. The inner insulating member is provided with multiple pairs of outward-radiating splines on its outer diameter that extend longitudinally the length of inner insulating member. Inward-radiating splines on outer insulating member mate with outward-radiating splines on inner insulating member in an interlocking fashion to thereby form multiple lumens between adjacent sets of mated inward- and outward-radiating splines. The interlocking splines provide isolation of conductors that may be running through each lumen. The number of lumens and their general size and shape are determined by the number of interlocking splines and the geometry of outer and inner insulating members such that multiple lumens may be provided to accommodate a desired number of conductors that may vary in size.

Interaction of inward radiating splines with outward radiating splines produces efficient torque transfer between the outer and inner insulating members and down the length of the elongated body. The materials from which the inner and outer members are formed may be selected to tailor the medical device with a desired degree of torque transfer properties and stiffness or flexibility in bending. During assembly, conductors may be laid in grooves formed between pairs of outward radiating splines on the inner insulating member. The outer insulating member may then be positioned such that inward-radiating splines are aligned with outward-radiating spline pairs. The outer insulating member is then advanced over the inner insulating member such that multiple conductors are assembled within multiple lumens simultaneously.

In one embodiment, a steerable, navigable guide catheter is provided with a splined, multilumen catheter body in accordance with the present invention. The inner insulating member is provided with at least one central lumen through which a medical therapy or device may be delivered. The catheter may include one or more, preferably four, location sensors spaced axially from one another along a distal segment of the catheter. Each location sensor is provided with an associated conductor extending through one of the multiple lumens formed by the outer and inner insulating members. When location sensors are provided as electromagnetic sensors, conductors are preferably provided as twisted pairs to shield against voltage inductions along the conductor when an external electromagnetic field is applied. Preferably the outer insulating member is not reinforced with metallic braiding in the distal region of the catheter to avoid shielding the electromagnetic location sensors.

One or more pull wires may extend from a proximal manipulative handle to or near the distal catheter end through one or more of the multiple lumens to aid in steering the catheter through a vascular pathway. The navigable guide catheter may further include one or more electrodes or other physiological sensors located along the catheter body or at its distal end, each having an associated conductor extending through one of the multiple lumens.

In alternative embodiments, one or more fluid delivery needles may be carried in one or more lumens of the multilumen body. Fluid delivery needles may be used to deliver a pharmaceutical, genetic or biologic agent to a targeted body tissue site by actuating the needles at a proximal end to cause the needles to advance and extend from the distal end of the catheter into a targeted site. Needles may extend at acute angles away from the central axis of the multilumen body and thereby allow delivery of a fluid agent to a relatively large volume of tissue and to further act as an anchoring mechanism to maintain the distal end of the multilumen body at a tissue site.

In another embodiment, a multipolar cardiac lead is provided with a splined, multilumen lead body in accordance with the present invention. The lead may be provided with any combination of a tip electrode, and/or one or more ring electrodes, and/or one or more coil electrodes each with an associated conductor extending through one of the multiple lumens of the lead body. An open lumen may optionally be provided for receiving a guide wire or stylet.

To achieve precise steering of a multilumen body as it is advanced along an internal body pathway, multiple steering members may be provided that are attached at different longitudinal locations along the distal end of the multilumen body to impose varying degrees of curvature to the distal end in different directions. Paired steering members may be arranged to act as antagonistically to deflect the multilumen body in opposite directions. In alternative embodiments, a steerable multilumen body may include a sensor, such as an ultrasonic, force or torque transducer, which produces a feedback signal that provides information regarding surrounding tissue structures or obstructions. This information may aid a user in advancing the multilumen body to a desired site.

The multilumen body provided by the present invention thus provides a versatile platform in which various combinations of conductors, steering members, sensors, or open delivery lumens may be incorporated for use in medical device or therapy delivery procedures or diagnostic procedures. Torque transfer and bending flexibility may be uniquely tailored to specific applications through careful selection of inner and outer insulating member materials. The multilumen body may be readily assembled with multiple conductors, sensors, wires, steering members, or other elements within respective lumens.

FIG. 1 is a cross-sectional view of a multilumen body according to the present invention. As illustrated in FIG. 1, a multilumen body 10 according to the present invention includes an outer insulating member 12 and an inner insulating member 14. Outer insulating member 12 is a generally tubular member having a generally round outer wall 13 having a corresponding outer diameter, and an inner wall 15 having multiple, radially inward extending members 16a through 16f positioned along at least a portion of the length, and preferably the entire length, of outer insulating member 12. Inner insulating member 14 is provided with a corresponding number of paired, radially outward extending members 18a through 18l, with each pair of outward extending members 18a through 18l forming a groove or slot 19 that receives one of inward extending member 16a through 16f so that inward extending members 16a through 16f of outer insulating member 12 interlock with outward extending members 18a through 18l of inner member 14. Inner insulating member 14 is a solid structure, or preferably, a generally tubular structure having at least one generally central, inner lumen 22 through which a medical device or therapy may be delivered. Inner insulating member 14 may alternatively include multiple, inner lumens.

The interlocking splined construction of multilumen body 10 provides efficient torque transfer from the outer insulating member 12 to the inner insulating member 14 while still allowing for high flexibility if desired. Torque applied to outer insulating member 12 at a proximal end of elongated multilumen body 10 will be efficiently transferred to the inner insulating member 14 and to a distal end of multilumen body 10. Furthermore, the splined construction is highly kink-resistant reducing the need for reinforcing braiding in the body walls.

When assembled as shown in FIG. 1, multiple lumens 20a through 20f are formed between the outer insulating member 12 and inner insulating member 14, between adjacent sets of mated inward extending members 16a through 16f and outward extending members 18a through 18l so that each adjacent pair of outward extending members 18a through 18l is separated by a corresponding one of lumens 20a through 20f. In particular, as illustrated in FIG. 1, slots or groove portions 21 are formed along inner insulating member 14 between adjacent paired outward extending members 18a through 18l, so that lumens 20a through 20f are formed by slots 21 and inner wall 15 of outer insulating member 12. For example, lumen 20a is formed by inner wall 15 and slot 21 between paired outward extending members 18a and 18b and adjacent paired outward extending members 18c and 18d.

Each lumen 20a through 20f may carry a conductor, cable, wire, steering member, or other elongated member to an associated component, which may be a sensor, electrode, or other component, located along the length of the body 10 or at a distal end of body 10. The number of splines provided on outer insulating member 12 and inner insulating member 14 by inward extending members 16a through 16f and outward extending members 18a through 18l may be adapted to the number of lumens required for a particular application.

It is understood that, although shown in FIG. 1 as having a generally rounded geometry, inward extending members 16a through 16f and outward extending members 18a through 18l may alternatively be formed having any interlocking geometry that is practical to manufacture. A generally rounded geometry is preferred because it is practical for extrusion methods that may be used for forming inner and outer insulating members 14 and 12. In an alternative embodiment, outer insulating member 12 may be provided with pairs of inward-radiating splines, which mate with a corresponding outward radiating spline on inner insulating member 14. In other embodiments, multiple sets of two or more inward-radiating splines may mate with multiple sets of two or more outward-radiating splines.

Inner and outer insulating members 14 and 12 are preferably formed by extruding a biomedical grade polymer through an appropriately shaped die. Considerations taken into account in selecting a polymer for fabricating inner and outer insulating members 14 and 12 include: rigidity and stiffness required for torque and force transfer; flexibility and elasticity required for steerability and adaptability to a tortuous pathway such as within the cardiovascular system; low-surface friction within lumens through which medical devices will be passed through; and high-surface friction between interacting splines for structural stability of body 10 and for isolating lumens carrying conductors. When used acutely, the inner and outer insulating members 14 and 12 may be formed from an extruded nylon, polyether block amide, thermoplastic polyurethane, thermoplastic polyester, polyketone or fluoropolymer such as polytetrafluoroethylene. An advantage of the present invention is that different materials may be selected for fabricating inner and outer insulating members 14 and 12 thus allowing precise tailoring of torque transfer properties, flexibility, surface friction, or other properties for a specific application.

It is recognized that outer insulating member 12 may optionally include reinforcing braiding. Reinforcing braiding may be incorporated in outer member 12 by extruding a first layer onto an appropriately shaped mandrel, winding braiding over the first layer in a continuous reel-to-reel process, then extruding a second layer over the braiding.

Figure 2:
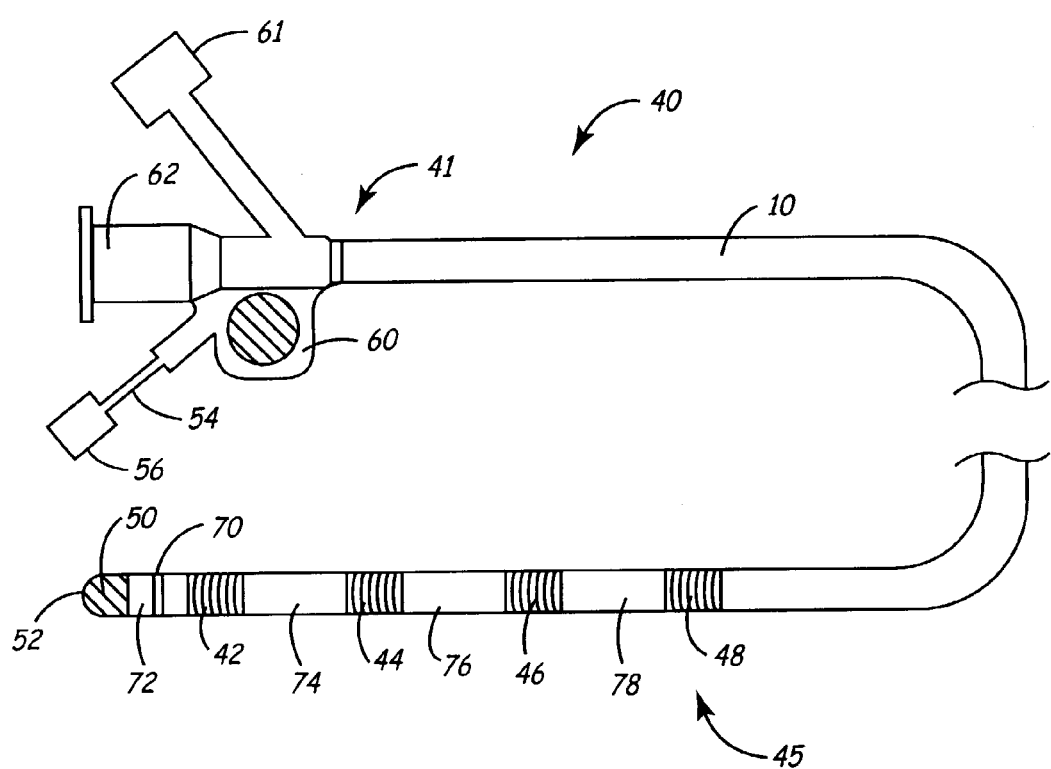
FIG. 2 is a plan view of a navigable guide catheter provided with a multilumen lead body including splined inner and outer insulating members in accordance with the present invention.

FIG. 2 is a plan view of a navigable guide catheter provided with a multilumen lead body including splined inner and outer insulating members in accordance with the present invention. As illustrated in FIG. 2, catheter 40 is a navigable, steerable catheter having a manipulative handle 60, a shielded connector 61, and an access hub 62 at a proximal end 41 of catheter 40. Multiple location sensors 42, 44, 46 and 48 are affixed along a distal end 45 of catheter 40 and spaced axially from one another. In a preferred embodiment, location sensors 42, 44, 46, and 48 are provided as electrically conductive coils formed from fine copper wire in which current is induced by an electromagnetic source located externally to the patient. If braiding is included in outer insulating member 12, it is preferably terminated proximal to sensor 48 to avoid shielding sensors 42, 44, 46 and 48. The use of electromagnetic coils as location sensors on a navigable catheter is generally disclosed in co-pending U.S. patent application Ser. No. 10/299,969 to Hunter et al., entitled "Navigation System for Cardiac Therapies", incorporated herein by reference in its entirety. Each coil is preferably on the order of 100 to 1000 turns, more preferably 200 to 750 turns, of fine, insulated copper wire approximately 0.0012 inches in diameter. However, the number of turns and diameter of the wire may vary depending on the application. An advantage of the present invention is that relatively large coils having approximately the same outer diameter as the catheter body 10 may be provided allowing for good coupling with an externally-applied electromagnetic field. In other embodiments, other location or mapping sensors known in the art may be provided. For example, mapping electrodes may be provided for measuring a voltage signal having components corresponding to three orthogonal current signals applied through the patient as generally disclosed in U.S. Pat. No. 5,983,126 issued to Wittkampf, hereby incorporated herein by reference in its entirety.

An end cap member 50 seals the distal end 45 of the multiple lumens of body 10 against the ingress of body fluids. End cap member 50 is formed from a biocompatible polymer material and may be over-molded onto the distal end of body 10. End cap member 50 is provided with an opening 52 to a generally central lumen (not shown in FIG. 2) extending within catheter body 10 such that a medical device or therapy delivered through the central lumen may exit opening 52.

End cap member 50 may alternatively be formed from a conductive biocompatible metal, such as stainless steel, platinum, iridium, titanium, or alloys thereof, and serve as an electrode for sensing cardiac signals, or other electrophysiological signals. Catheter 40 may alternatively or additionally be equipped with additional electrodes or one or more sensors of other types of physiological signals. Other types of physiologic sensors that may be included on catheter body 10 include absolute pressure sensors, temperature sensors (thermocouple or infrared), oxygen sensors, pH sensors, acoustical sensors, etc.

Figure 3:
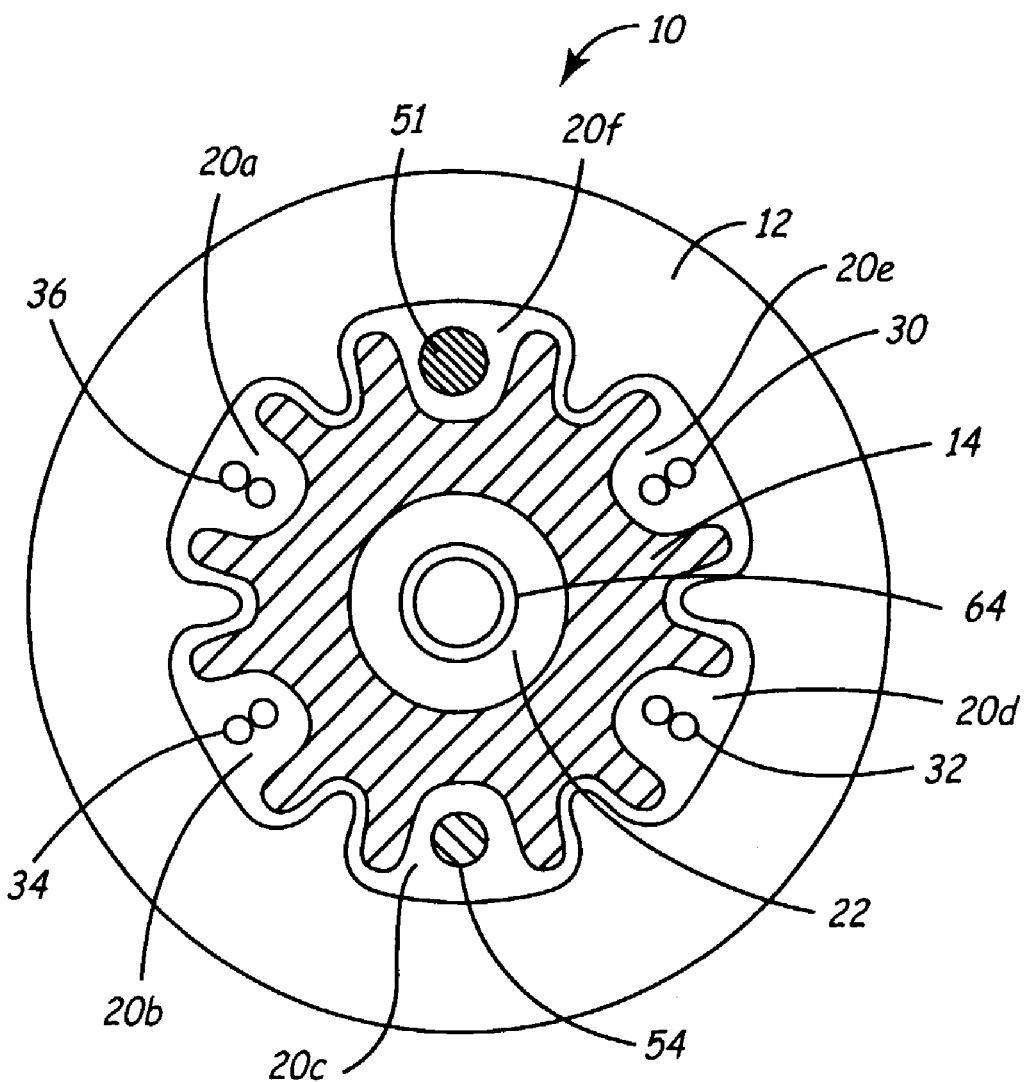
FIG. 3 is a sectional view of an arrangement of conductors within the multilumen body included in the guide catheter of FIG. 2.

FIG. 3 is a sectional view of an arrangement of multiple conductors within multilumen body 10 included in guide catheter 40. Inner insulating member 14 is provided with a generally central, open lumen 22 through which a medical device 64 or medical therapy may be delivered. Open lumen 22 is accessible via access hub 62 (shown in FIG. 2) at the proximal end 41 of body 10. For example, medical device 64 shown in FIG. 3 is a hollow needle for use in delivering of a pharmaceutical, genetic, or biologic agent in a liquid medium. However, according to the present invention, other medical devices, such as cardiac pacing or defibrillation leads, ablation catheters, sensors, etc. may alternatively or additionally be delivered through lumen 22. Thus catheter 40 may serve multiple purposes during a diagnostic and/or therapy delivery procedure.

A conductor 51 that extends through lumen 20*f* is electrically coupled to end cap member 50, which, in this embodiment, also serves as an electrode. Each of four pairs of twisted conductors 30, 32, 34 and 36 extend through a respective lumen 20*a*, 20*b*, 20*d*, and 20*e* to one of location sensors 42, 44, 46, and 48. Proximal ends of conductors 30, 32, 34, 36 and 50 are coupled to shielded connector assembly 61 (shown in FIG. 2). Connector assembly 61 is provided for connection of catheter 40 to an external monitor or sensor interface for monitoring signals received from location sensors 42, 44, 46, and 48 and electrode 50. Catheter 40 is intended for use with an image-guided navigation system such as the system generally disclosed in co-pending U.S. patent application Ser. No. 10/299,969 to Hunter et al., entitled "Navigation System for Cardiac Therapies".

A pull wire 54 extends through lumen 20*c*. Pull wire 54 may be provided as a high-tensile grade stainless steel wire that is fixedly attached at or near distal end 45 of guide catheter 40. An anchoring member 70 (FIG. 2) is a generally ring shaped member encircling the outer circumference of body 10 near the distal end 45 of catheter 40. Pull wire 54 may be fixedly attached, by welding or other appropriate bonding or joining methods, to anchoring member 70. Anchoring member 70 may optionally serve as an electrode with pull wire 54 serving additionally as a conductive element to carry electrical current between anchoring member 70 and a proximal connector 61.

Pull wire 54 extends from proximal manipulative handle 60 in FIG. 2 to anchoring member 70 and is provided with a grip 56 for applying tension to pull wire 54 to cause deflection of distal end 45 of catheter 40. A manipulative handle and pull wire system for steering catheter 40 may be provided. When a pull wire 54 or other steering mechanism is included in guide catheter 40, the distal end 45 of catheter body 10 shown in FIG. 2 is preferably provided with relatively greater flexibility than the remainder of catheter body 10. Outer insulating member 12 includes outer insulating segments 72, 74, 76, and 78 positioned along distal end 45 of multilumen body 10, which are preferably formed from a lower durometer polymer than the remainder of catheter body 10.

Figure 4:
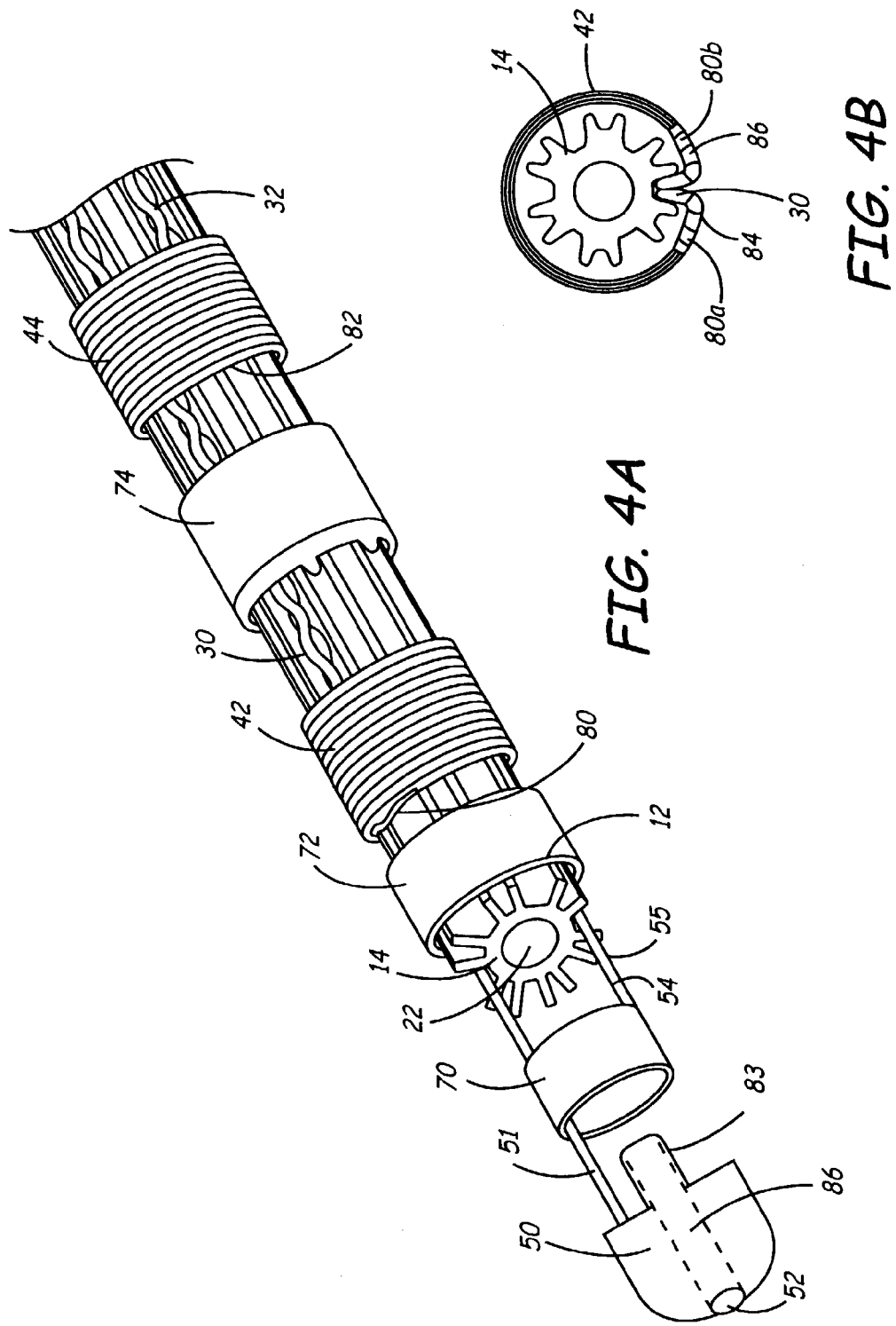
FIG. 4A is an exploded view of a portion of the distal end of the navigable guide catheter of FIG. 2.
FIG. 4B is an end view of an electromagnetic location sensor included in the catheter of FIG. 2 illustrating one method for electrically coupling the coil windings of the sensor to a twisted pair conductor.

FIG. 4A is an exploded view of a portion of the distal end 45 of navigable guide catheter 40. Assembly of the distal end 45 includes coupling of each location sensor 42, 44, 46 and 48 (46 and 48 not visible in this view) to corresponding twisted pair conductors 30, 32, 34 and 36 (34 and 36 not visible in this view). A distal segment 80 of each wire included in twisted pair 30 is stripped of insulation and extended along the distal end of sensor 42 and electrically coupled to sensor 42.

FIG. 4B is an end view of an electromagnetic location sensor illustrating one method for electrically coupling the coil windings of the sensor to a twisted pair conductor. A portion of one end 84 of the fine copper wire used to form the coiled sensor 42 is wrapped in a generally helical fashion around the distal segment 80*a* of one wire included in twisted pair conductor 30. The opposite end 86 of the fine copper wire used to form coiled sensor 42 is wrapped around the distal segment 80*b* of the second wire included in twisted pair conductor 30. The conductor wire segments 80*a* and 80*b* and coil wire ends 84 and 86 may then be welded or soldered to reinforce the coupling between conductor 30 and coiled sensor 42 by capturing the ends 84 and 86 in the weld pool. In FIG. 4A, a distal segment 82 of each wire included in twisted pair 32 is stripped of insulation and extended along and electrically coupled to the distal end of sensor 44 in the manner shown in FIG. 4B. Sensors 46 and 48 are similarly coupled to twisted pair conductors 34 and 36 (not shown).

Sensors 42, 44, 46 and 48 are then passed over inner insulating member 14 in an alternating fashion with distal outer segments 72, 74, 76 and 78 such that each sensor is captured between outer segments as shown in FIG. 2. In FIG. 4A, sensor 42 is captured between distal outer segments 72 and 74. One or more of the outer insulating segments 72, 74, 76 and 78 may optionally be provided without inward extending members 16*a*-16*f* in order to enhance the flexibility of the distal end 45 to ease steering of the multilumen body 10. Enhanced flexibility, however, is provided at the expense of reduced torque transfer along that segment. For example, according to a preferred embodiment of the present invention, inward extending members 16*a*-16*f* are included in outer insulating members 74, 76, and 78 but are not included in outer insulating member 72.

Once assembled onto inner insulating member 14, sensors 42, 44, 46 and 48 are encapsulated by applying a medical grade adhesive over the outer surface of sensors 42, 44, 46 and 48 to seal sensors against corrosive body fluids and bond sensors to catheter body 10. An adhesive for sealing sensors 42, 44, 46 and 48 is preferably curable with ultraviolet light. Outer insulating segments 72, 74, 76 and 78 along distal end 45 are therefore preferably formed from a polymer material lacking fillers or colorants that would otherwise limit the transmission of ultraviolet light through outer insulating segments 72, 74, 76 and 78 of outer insulating member 12. However, other types of medical grade adhesives may be used successfully for bonding and encapsulating the sensors 42, 44, 46 and 48, such as urethane, epoxy or silicone adhesives. Parylene, a thermoplastic polymer that is a highly crystalline, straight chain compound with low gas permeability may also be used as a bonding compound. Depending on the sensor type and size that is utilized, the materials and methods of sealing, bonding and encapsulating the sensors become very important in ensuring a stable structure.

To prevent pull wire 54 from becoming adhesively bonded to inner insulating member 14 during the encapsulation of sensors 42, 44, 46 and 48, at least the distal segment of pull wire 54 extending through sensors 42, 44, 46 and 48 is provided within a thin-walled sleeve 55. Sleeve 55, which is formed of a polymeric material, preferably a polyimide, provides a clearance lumen through the opening of sensors 42, 44, 46 and 48 that allows relative motion between pull wire 54 and the sensors.

The remainder of catheter distal end 45 is assembled by assembling pull wire 54 and end cap member 50 on distal end 45. Pull wire 54 is welded, soldered or mechanically joined to an anchoring member 70. Anchoring member 70 is inserted over the outer diameter of distal outer segment 72, as shown previously in FIG. 2, or alternatively may be inserted into outer segment 72, over the outer wall 13 of inner insulating member 14. Conductor 51 is electrically coupled to end cap member 50 so that end cap member 50 may also serve as an electrode. End cap member 50 is shown having a proximal tubular extension 83 that is insertable within inner lumen 22 through anchoring member 70. A lumen 86, indicated by dashed line, within end cap member 50, extends from distal opening 52 through extension 83, and allows a medical device or therapy being delivered through inner lumen 22 to exit the distal end 45 of catheter 40.

Figure 5:
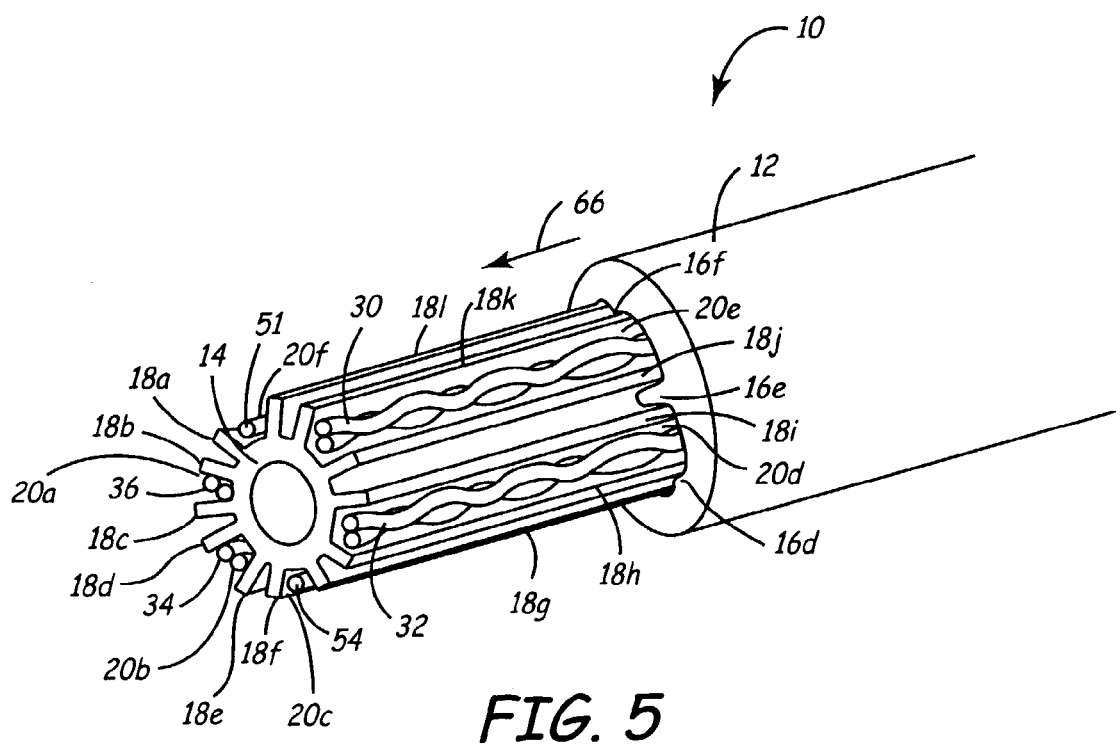
FIG. 5 is a perspective view showing the assembly of the multilumen body of FIG. 3.

After assembling the distal end 45 of catheter 40, the remainder of catheter body 10 may be assembled. FIG. 5 is a perspective view showing the assembly of outer insulating member 12 over inner insulating member 14. Each twisted pair conductor 30, 32, 34, and 36 and conductor 51 and pull wire 54 is positioned within a respective groove insulating member corresponding to a portion of lumens 20*a* through 20*f* defined by inner insulating member 14. Outer insulating member 12 is then advanced over inner insulating member 14 in the direction of arrow 66 after aligning inward extending members 16*a* through 16*f* (16*a* through 16*c* not visible in FIG. 5) with corresponding slots formed by pairs of outward extending members 18*a* through 18*l*. The interlocking inward extending members 16*a* through 16*f* and outward extending members 18*a* through 18*l* prevent conductors 30, 32, 34, 36 and 50 and pull wire 54 from inadvertently crossing between lumens 20*a* through 20*f* during assembly. In this way, the two-piece, splined multilumen body 10 of the present invention allows multiple conductors to be assembled within multiple lumens simultaneously in a relatively easy manner compared to threading multiple conductors one at a time through respective lumens.

Figure 6A:
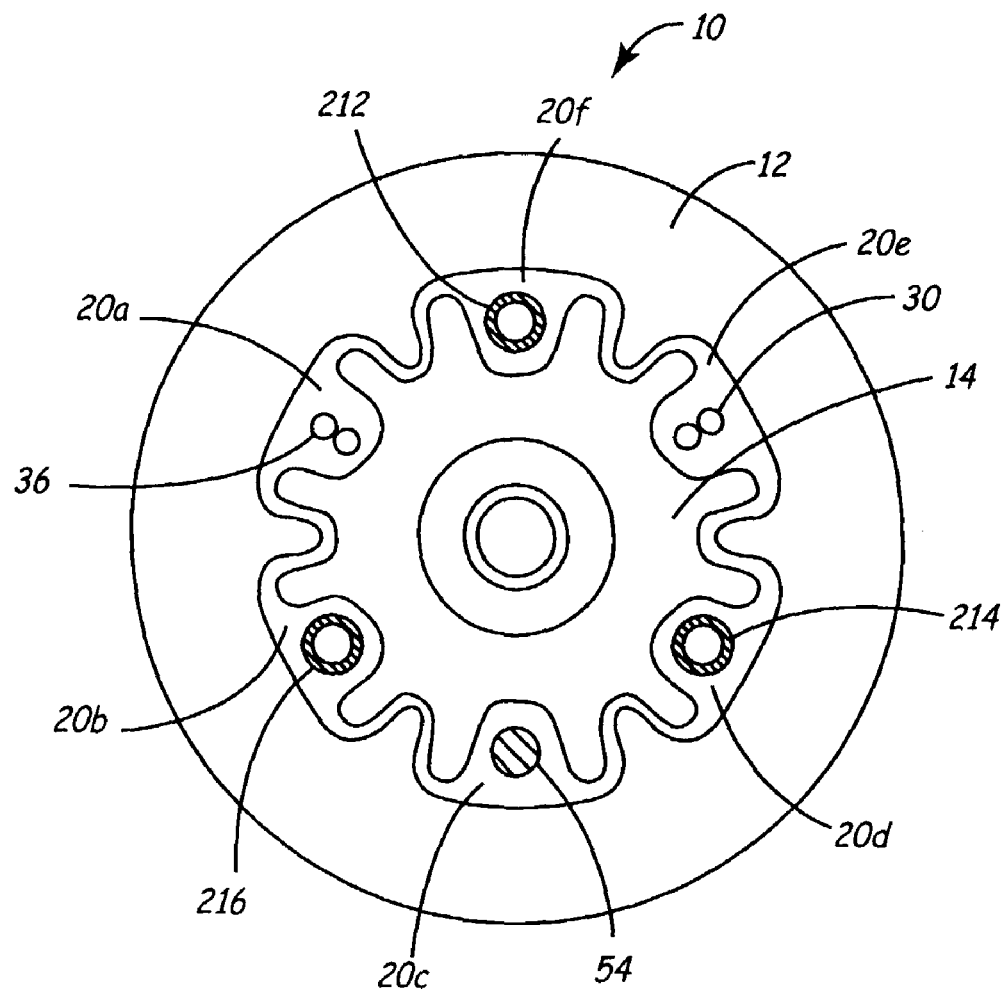
FIG. 6A is a sectional view of an alternative embodiment of a navigable guide catheter having a multilumen body carrying multiple fluid delivery needles.

FIG. 6A is a sectional view of an alternative embodiment of a navigable guide catheter having a multilumen body carrying multiple fluid delivery needles. As illustrated in FIG. 6A, according to an alternate embodiment of the present invention, multilumen body 10 includes three hollow needles, 212, 214 and 216 extending through three lumens 20*b*, 20*d*, and 20*f* of multilumen lead body 10. In this embodiment, two twisted pair conductors 30 and 36 associated with electromagnetic sensors (not shown) and a pull wire 54 are shown extending through the remaining lumens 20*e*, 20*a*, and 20*c*, respectively. Hollow needles 212, 214, and 216 may be used for delivering a pharmaceutical, genetic or biologic agent in a liquid medium. Needles 212, 214, and 216 may be actuated by a handle (not shown) located at the proximal end of multilumen body 10 to cause advancement and retraction of needles 212, 214 and 216 into and out of body tissue. Multiple needles may be used through multiple lumens of body 10 to advantageously deliver an agent to a larger volume of tissue than is possible by using a single needle extended axially out the distal end of a catheter.

Sealing and isolating individual lumens 20*a*-20*f* is important in maintaining electrical isolation of conductors and unimpeded movement of needles 212, 214 and 216 and pull wire 54 through respective lumens. Careful material selection for fabricating outer and inner insulating members 12 and 14 allows zero tolerance between mated outer and inner insulation splines and provides interference between splines for effectively isolating and sealing individual lumens.

Figure 6B:
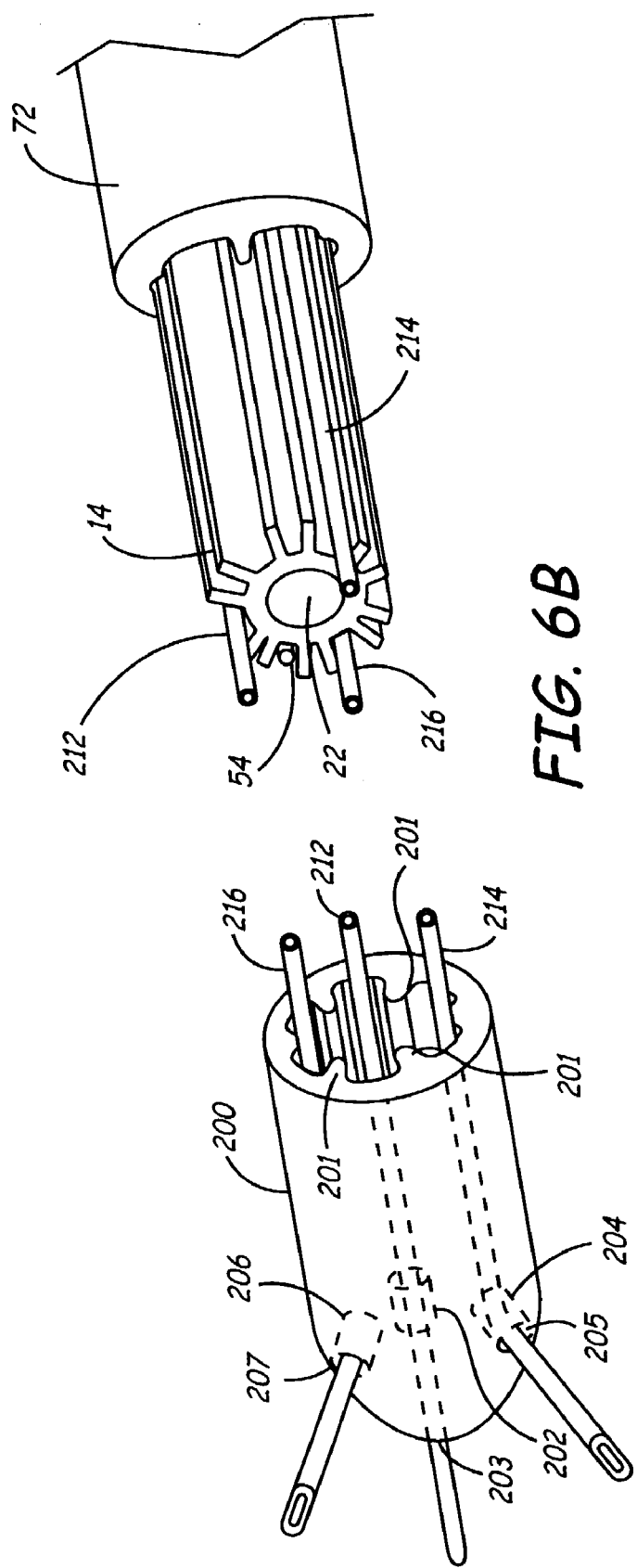
FIG. 6B is a perspective view of the distal end of the multilumen body of FIG. 6A and an end cap member for use with multiple fluid delivery needles.

FIG. 6B is a perspective view of the distal end 45 of multilumen body 10 and an end cap member 200 for use with multiple fluid delivery needles. End cap member 200 is provided with inward extending members 201 for mating with the distal end of inner insulating member 14, similar to outer insulating member 12. Distal outer insulation segment 72 and end cap member 200 are bonded using an appropriate adhesive at a butt joint when assembled. Pull wire 54 is fixedly attached to an anchor member (not shown) as described previously. End cap member 200 includes three needle guide lumens 202, 204 and 206 for receiving and guiding hollow needles 212, 214, and 216 through end cap member 200 and out the distal end of cap member 200 through distal openings 203, 205 and 207. In alternative embodiments, one or more needle guide lumens may be included in end cap member 200 for guiding one or more needles in a desired direction into body tissue. Needle guide lumens 202, 204 and 206 are angled to direct needles 212, 214 and 216 at a desired angles from each other as needles 212, 214 and 216 exit openings 203, 205, and 207, which may be in the range of zero degrees (to extend needles in parallel) to less than 90 degrees with respect to the central axis of end cap member 200. In the embodiment shown in FIG. 6B, needle guide lumen 202 is formed along the center axis of end cap member 200 to direct the advancement of needle 212 axially out central opening 203. Guide lumens 204 and 206 are angled approximately 30 degrees relative to the central axis of cap member 200 and 60 degrees from each other to direct the advancement of needles 214 and 216 out openings 205 and 207 at angles away from the central axis of multilumen body 10. Needles 212, 214 and 216 are preferably formed from a superelastic nitinol, low modulus titanium or other material that allows needles 212, 214, and 216 to conform to the angled geometry of guide lumens 202, 204, and 206 and extend linearly when not constrained by guide lumens 202, 204, and 206.

By directing needles 212, 214 and 216 in different directions, the present invention enables a relatively larger volume of tissue to be treated by a fluid agent than when needles are advanced in parallel. Furthermore, needles penetrating the tissue at angles, for example as shown in FIG. 6B, act to anchor the end cap member at a desire tissue site. When put to use, the steerable, navigable catheter is advanced to a desired tissue site, and hollow needles 212, 214, and 216 are advanced into the body tissue using an actuator located at the proximal end of the catheter. Needles 212, 214 and 216 provide an anchoring mechanism for maintaining the position of the catheter at the desired tissue site while a fluid agent is injected into the body tissue through needles 212, 214 and 216. After therapy administration is complete, the needles 212, 214 and 216 are retracted back into end cap member 200 through openings 203, 205, and 207, and the catheter is moved to another treatment site or removed from the patient's body.

FIG. 6C is a plan view of the distal end of a navigable catheter having a multilumen body including a fluid delivery needle that may additionally serve as an anchoring mechanism. Identically numbered components correspond to those in FIG. 2. As illustrated in FIG. 6C, in an extended position, a hollow needle 215 extends outward from an opening 217 in distal outer insulation segment 72'. Needle 215 is actuated at a proximal end such that needle 215 is extended and retracted from distal segment 72'.

Figure 6D:
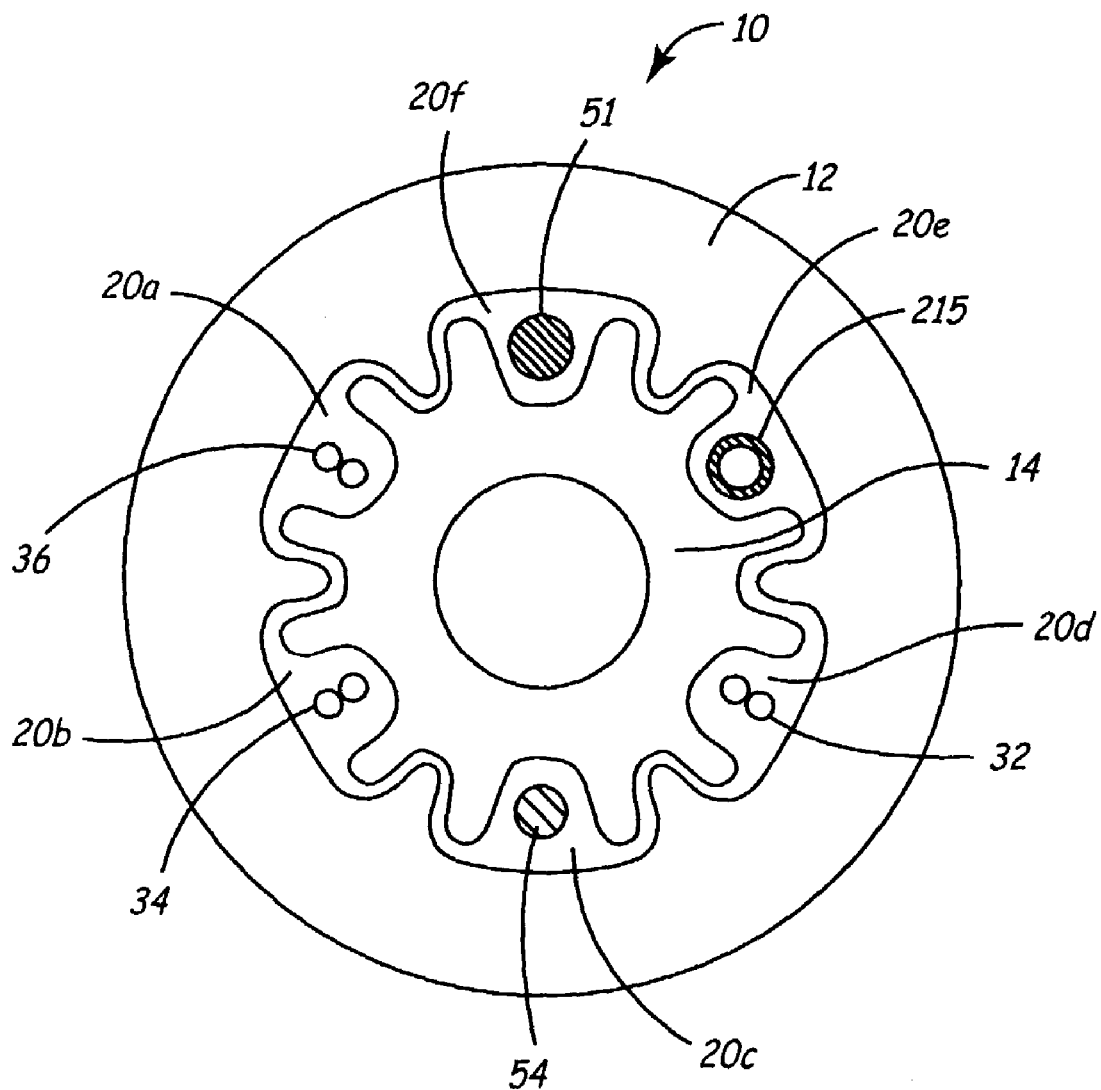
FIG. 6D is a sectional view of the multilumen body of FIG. 6C.

FIG. 6D is a sectional view of the multilumen body 10 of FIG. 6C. Identically numbered components correspond to those shown in FIG. 3, however, in this embodiment, hollow needle 215 replaces one twisted pair conductor in lumen 20e.

FIG. 6E is a partially exploded, perspective view of the distal end of the multilumen body of FIG. 6C. As illustrated in FIG. 6E, hollow needle 215 extends from lumen 20e of multilumen body 10 through a needle guide lumen 219 that traverses through the outer wall 13' of outer insulation segment 72'. Hollow needle 215 is advanced through lumen 20e and through guide lumen 219 to extend outward from body 10 at a predetermined angle, corresponding to the angle of guide lumen 219. In an extended position, as shown in FIGS. 6C and 6E, needle 215 penetrates a desired tissue site for the delivery of a fluid agent and additionally or alternatively serves as an anchoring mechanism to maintain the position of end cap member 52 while a medical device or therapy is delivered through open lumen 22 or while electrophysiological measurements are made when end cap member 52 also serves as an electrode. While a single needle is shown extending from distal segment 72', it is contemplated that multiple needles may be carried by multilumen body 10 and extend through multiple openings of outer insulation segment 72'.

Figure 7:
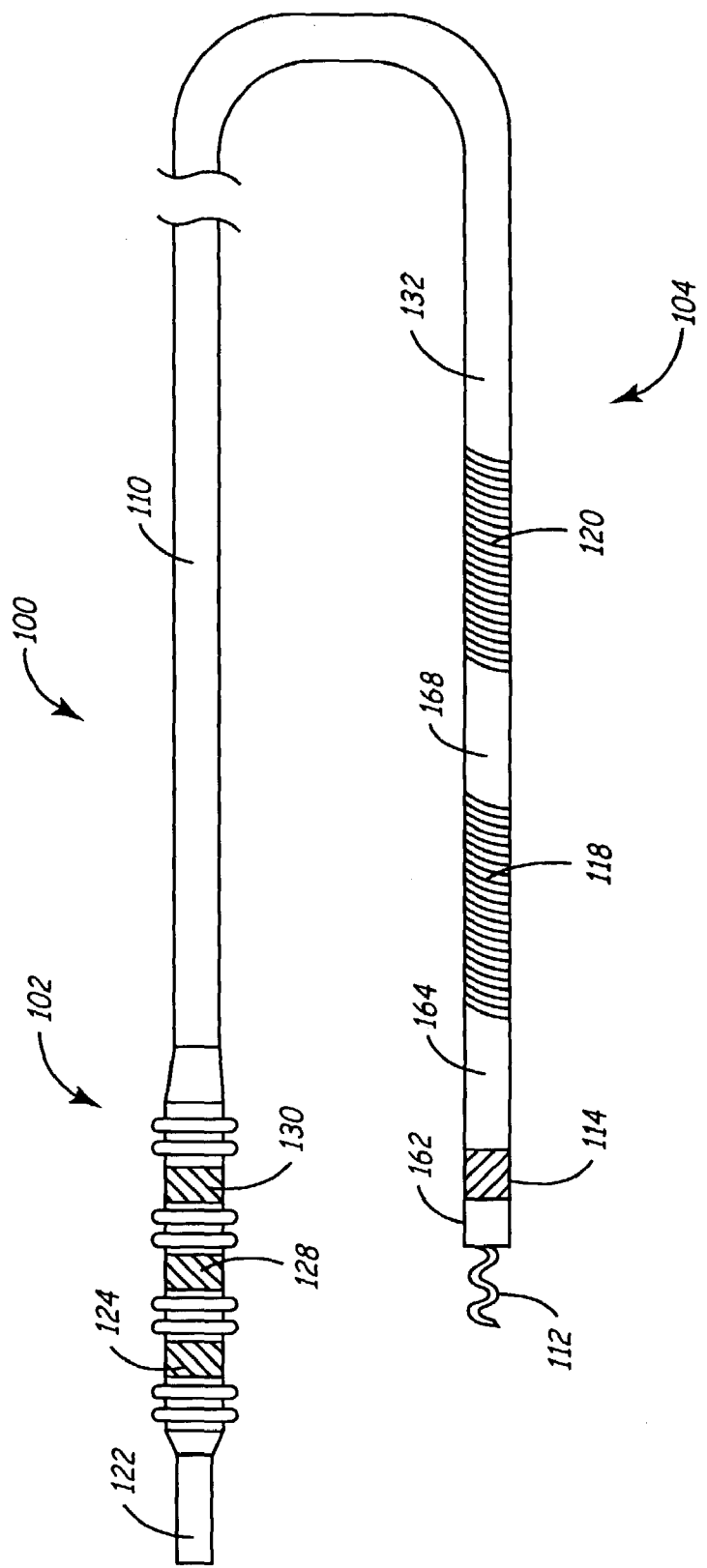
FIG. 7 is a plan view of a cardiac pacing and defibrillation lead constructed with a splined, multilumen lead body in accordance with the present invention.

FIG. 7 is a plan view of a cardiac pacing and defibrillation lead constructed with a splined, multilumen lead body in accordance with the present invention. As illustrated in FIG. 7, lead 100 is embodied as a quadrapolar lead having two defibrillation coil electrodes 118 and 120, a pacing tip electrode 112 and a ring electrode 114 for sensing cardiac signals or for bipolar pacing in combination with tip electrode 112. In alternative embodiments, lead 100 may be provided with any combination of a tip electrode, and/or one or more ring electrodes, and/or one or more coil electrodes or other types of sensors. Lead body 110 is provided as a splined, multilumen lead body for carrying multiple conductors extending between each of electrodes 112, 114, 118 and 120 and a proximal connector assembly 102, as described above. A connector assembly 102 at a proximal end of lead 100 includes a connector pin 122 associated with tip electrode 112 and connector rings 124, 128 and 130 corresponding with ring electrode 114 and coil electrodes 118 and 120. Tip electrode 112 is shown as an active fixation, helical electrode. Rotation of lead body 110 at its proximal end allows tip electrode 112 to be advanced into the myocardial tissue. Other types of tip electrodes know for use in cardiac leads, such as a barb or hook type electrode, a generally hemispherical electrode, or a tip ring electrode, may be included in alternative embodiments.

Figure 8:
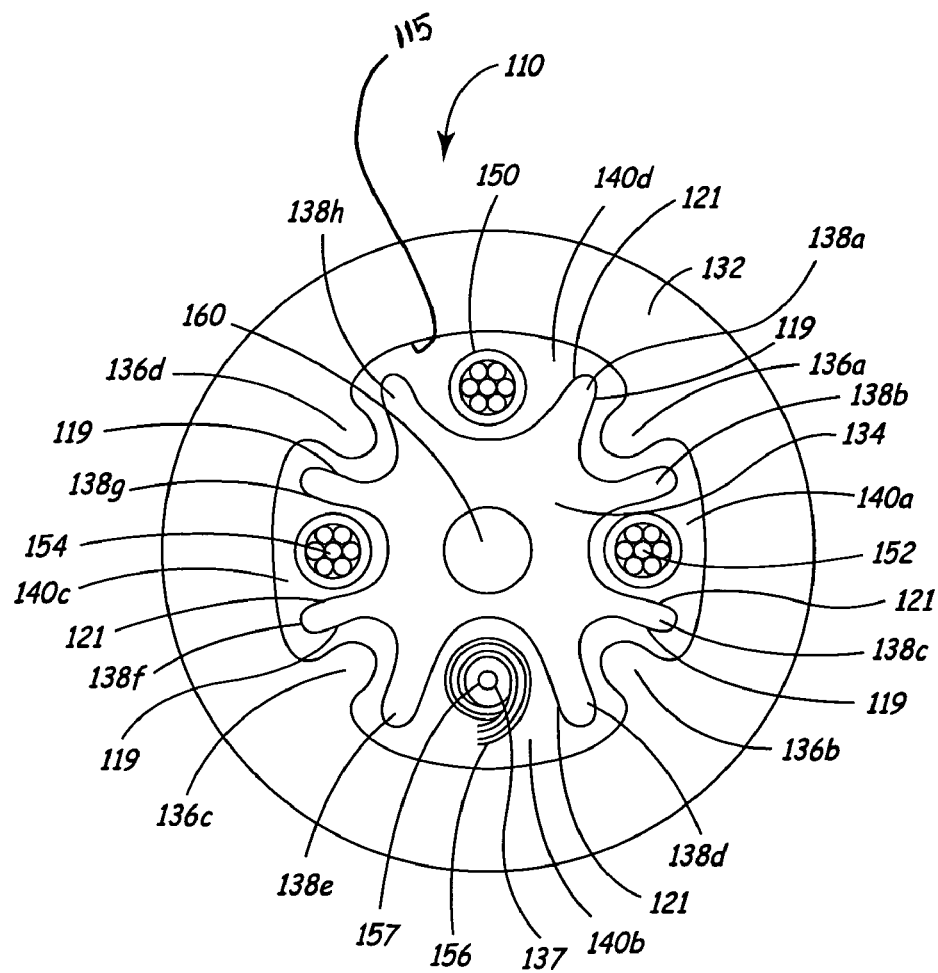
FIG. 8 is a sectional view of the lead body included in the lead of FIG. 7.

FIG. 8 is a sectional view of lead body 110. As illustrated in FIG. 8, lead body 110 is provided as a splined multilumen lead body having an inner insulating member 134 and an outer insulating member 132. Inner insulating member 134 includes multiple pairs of radially outward extending members 138a through 138h, each pair forming a groove or slot portion 119 that receives and interlocks with one of multiple radially inward extending members 136a through 136d positioned along an inner wall 115 of outer insulating member 132. Multiple lumens 140a through 140d are formed by inner insulating member 134 and outer insulating member 132, between adjacent sets of mated outward extending members 138a through 138h and inward extending members 136a through 136d. In particular, as illustrated in FIG. 8, slots or groove portions 121 are formed along inner insulating member 134 between adjacent paired outward extending members 136a through 136d, so that lumens 140a through 140d are formed by slot portion 121 and inner wall 115 of outer insulating member 132. For example, lumen 140a is formed by inner wall 115 and slot portion 121 between paired outward extending members 138a and 138b and adjacent paired outward extending members 138c and 138d.

In FIG. 8, four lumens are provided to carry four conductors in quadrapolar lead 100. However, the present invention is not intended to be limited to the formation of for lumens, but rather, a splined lead body according to the present invention may be provided having a corresponding number of mated splines for forming two, three or more lumens corresponding to the number of conductors required. The diameter of each lumen is determined by the geometry of inner and outer insulating members 134 and 132, which may be sized to accommodate a desired number of conductors of various diameters. Inner insulating member 134 may include a generally central inner lumen 160 for receiving a guidewire or stylet. Alternatively, an additional lumen formed between inner and outer insulating members 134 and 132 may be provided for receiving a guidewire or stylet.

Inner and outer insulating members 134 and 132 are preferably formed of a biocompatible polymer known for use in implantable leads, such as polyurethane or silicone. The material and its durometer may be selected to provide lead body 110 with desired physical properties such as flexibility, torque transfer, etc. Once advanced to an implant site, lead 110 must be rotated to engage helical tip electrode 112 in the myocardial tissue. Therefore in this embodiment, good torque transfer properties are desired. In other embodiments that do not include a helical tip electrode, greater flexibility may be more important than efficient torque transfer. Selection of outer and inner insulating members 132 and 134 may therefore be made to tailor lead body properties to a particular application.

For example, in one embodiment for providing enhanced torque transfer properties, inner insulating member 134 is formed from a polyketone, such as polyaryletherketone, available commercially under the tradename PEEK-Optima®, from Inyibio™, or polyetheretherketone available from Victrex-USA. The outer insulating member 132 may be formed from silicone with zero clearance between the inner and outer members 134 and 132, providing good isolation between conductor carried by lead body 110. Alternatively, the outer insulating member 132 may be formed from a urethane, such as Pellethane® 2363-55D available for Dow Chemical.

In FIG. 8, lumens 140a, 140c and 140d carry insulated conductors 150, 152, and 154 associated with ring electrode 114 and coil electrodes 118 and 120. Conductors may be provided as cabled conductors; drawn, brazed stranded conductors; straight wire conductors; mono- or multi-filar coiled conductors, or any type of conductor known for use in implantable medical leads. Lumen 140b carries a conductor 156, which may be provided as a multifilar coiled conductor, associated with tip electrode 112. A stylet or guide wire 137 may be advanced within a lumen 157 formed by coiled conductor 156 to aid in guiding lead 100 to an implant site. In an alternative embodiment, tip electrode 112 is an extendable/retractable helix, which is actuated by rotating coiled conductor 156 at a proximal end, which may correspond generally to an extendable helix disclosed in U.S. Pat. No. 4,106,512 issued to Bisping et al., incorporated herein by reference.

Figure 9:
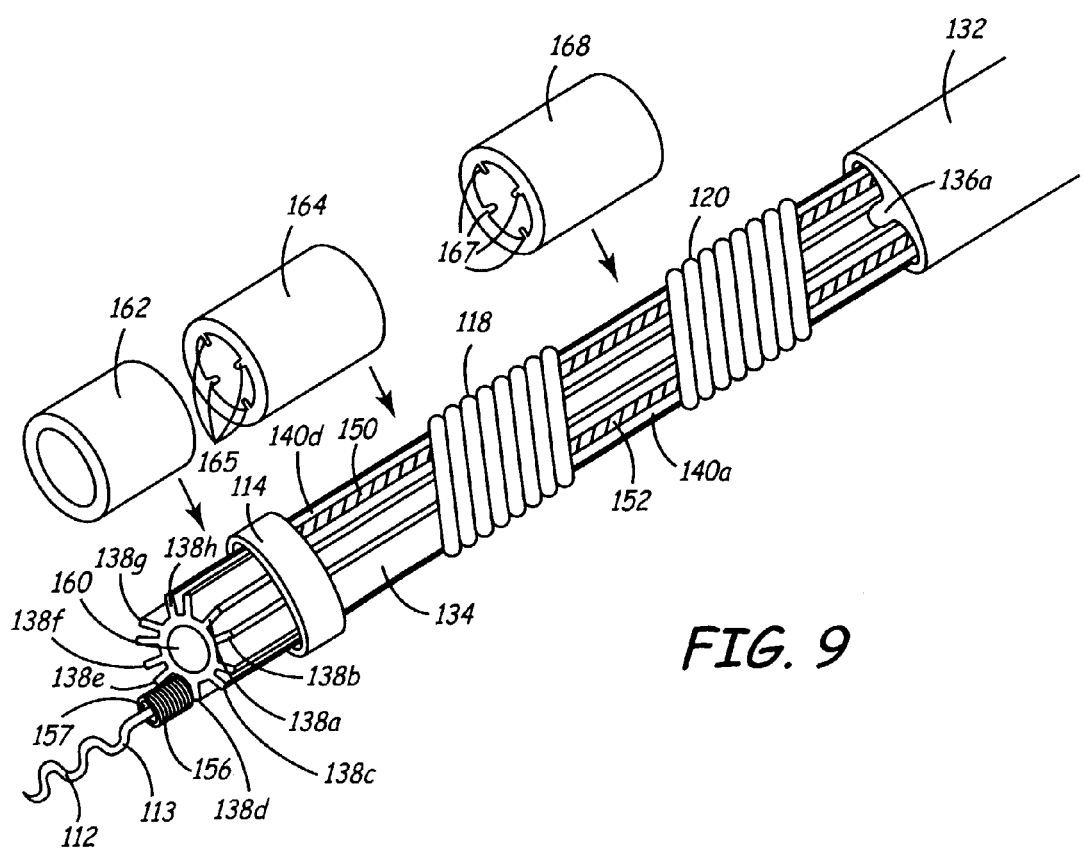
FIG. 9 is an exploded view of the distal end of the lead of FIG. 7.

FIG. 9 is an exploded view of the distal end 104 of lead 100. Lead 100 may be assembled in a manner as generally described above wherein conductors are first coupled to corresponding electrodes, which are then assembled onto the distal end of inner insulating member 134. As illustrated in FIGS. 8 and 9, coiled conductor 156 is coupled to tip electrode 112 by inserting a shank portion 113 of tip electrode 112 into lumen 157 and crimping, welding or otherwise coupling conductor 156 to electrode 112. Conductor 150 is coupled to ring electrode 114, by welding, crimping, staking, or an other appropriate method. Conductor 152 and conductor 154 (not visible in FIG. 9) are coupled to coil electrodes 118 and 120, respectively, according to methods known in the art. Coil electrode 120 is then passed over inner insulating member 134, followed by an outer insulating segment 168, coil electrode 118, outer insulating segment 164, ring electrode 114 and outer insulating segment 162. Outer insulating member 132 includes outer insulating segments 162, 164, and 168, with one or more of insulating segments 162, 164 and 168 including inward extending members 165 and 167 for mating with outward extending members 138a through 138f of inner insulating member 134, as described above. For example, as illustrated in FIG. 9, according to a preferred embodiment of the present invention, inward extending members 165 and 167 are included only within insulating segments 164 and 168 and are not included within insulating segment 162. However, according to the present invention, insulating segment 162 could include inward extending members and/or one of inward extending members 165 and 167 could be formed without inward extending members 165 and 167.

According to the present invention, each of conductors 150–156 are positioned within a respective slot portion 119 of lumens 140a-d formed by inner insulating member 134. Outer insulating segments 162, 164 and 168 of outer insulating member 132 are then advanced over inner insulating member 134, starting with outer insulating segment 168, to form the remaining portion of the lumen, and as a result, simultaneously capturing each conductor within a respective lumen. One advantage of the present invention is that the coil electrodes 118 and 120 assembled onto inner insulating member 134 may be approximately isodiametric with the outer diameter of outer insulation segments 164 and 168 and outer insulating member 132, creating a smooth lead profile. In prior art designs, a coil electrode is generally placed over the outer diameter of a lead body such that the coil electrode may protrude from the lead body creating a less desirable lead profile.

Figure 10A:
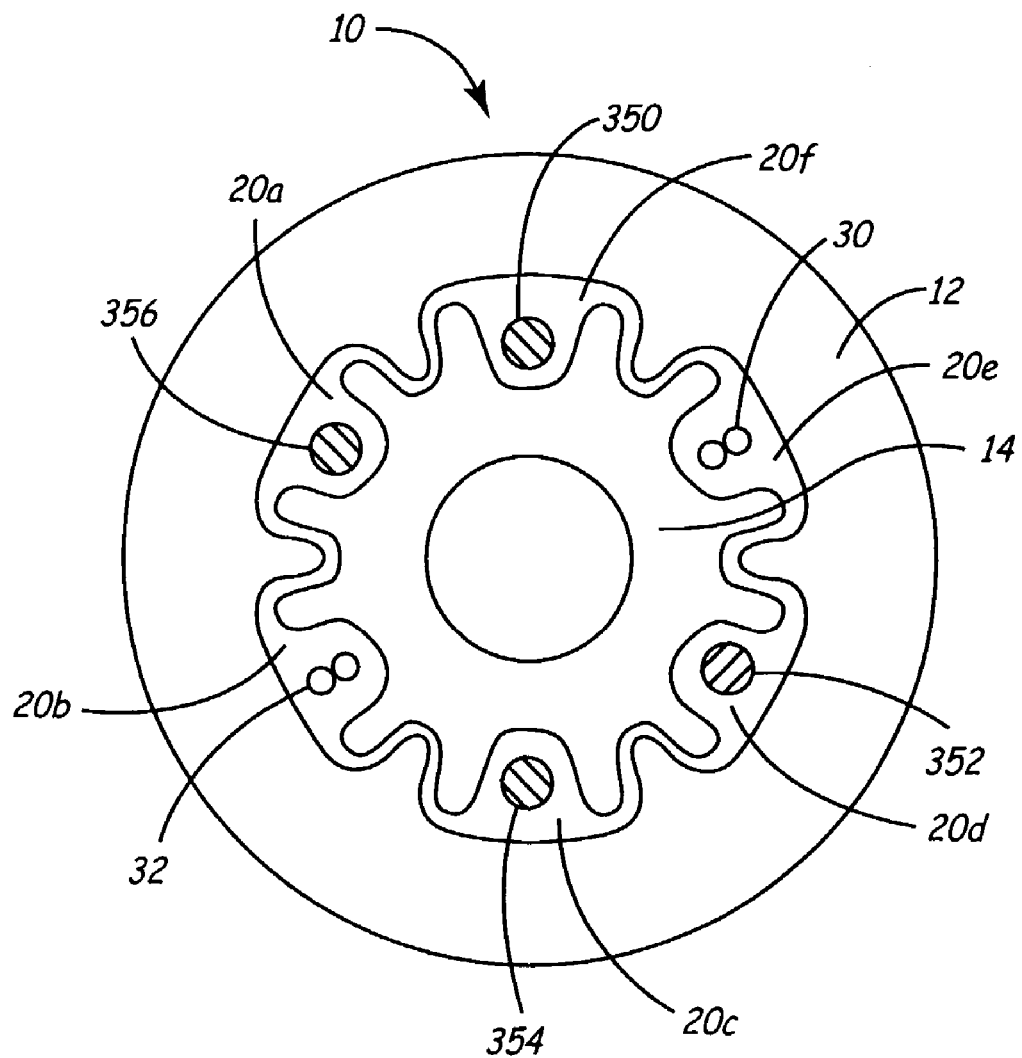
FIG. 10A is a sectional view of a multilumen body having multiple steering members in accordance with an alternate embodiment of the present invention.

FIG. 10A is a sectional view of a multilumen body having multiple steering members in accordance with an alternate embodiment of the present invention. According to an alternate embodiment of the present invention, in order to achieve precise steering during advancement of a multilumen body along an internal body pathway, multilumen body includes multiple steering members that are attached at different longitudinal locations along the distal end of the multilumen body to impose varying degrees of curvature at different points along the distal end. For example, as illustrated in FIG. 10A, four elongated steering members 350, 352, 354 and 356 are positioned within lumens 20a, 20c, 20d and 20f formed by inner insulating member 14 and outer insulating member 12. Steering members 350, 352, 354, 356 may be embodied as pull wires, elongated members formed using a shape memory alloy or polymer, or other deflecting mechanism known in the art. A selectively activated shape memory device that may be adapted for use with the present invention is generally disclosed in U.S. Pat. No. 6,323,459 issued to Maynard, hereby incorporated herein by reference in its entirety. Heat or electrically-activated shape memory materials may be used, however, if included, electrically-activated materials are preferred because other components carried by device 300, such as electromagnetic location sensors, may be sensitive to mechanical or functional degradation due to applied thermal energy. Steering members 350, 352, 354 and 356 are actuated at their proximal ends using a manipulative handle. Twisted pair conductors 30 and 32 are included in lumens 20b and 20e for use with two location sensors, for example.

Figure 10B:
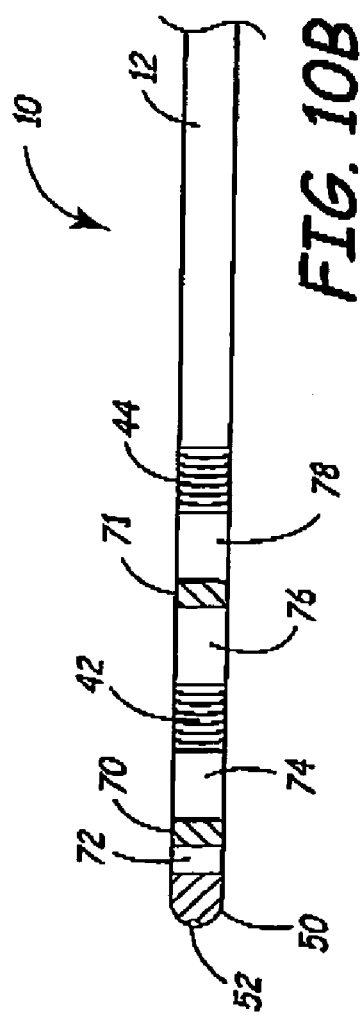
FIG. 10B is a plan view of the multilumen body of FIG. 10A in a non-deflected position.

FIG. 10B is a plan view of the multilumen body of FIG. 10A in a non-deflected position. As illustrated in FIG. 10B, multilumen body 10 includes two location sensors 42 and 44 coupled to twisted pair conductors 30 and 32 and two anchoring members 70 and 71 that are fixedly attached to steering members 350, 352, 354, and 356, as will be described below. Other components in FIG. 10B correspond to identically labeled components in FIG. 2.

Figure 10F:
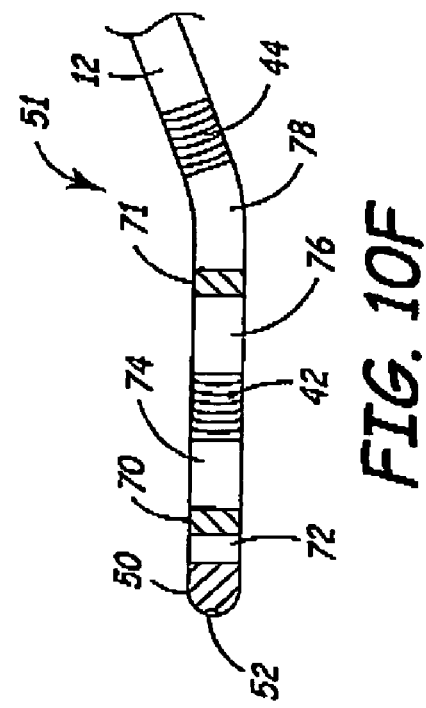
FIG. 10F is a plan view of a distal end of a multilumen body, according to the present invention, in a deflected position.
Figure 10H:
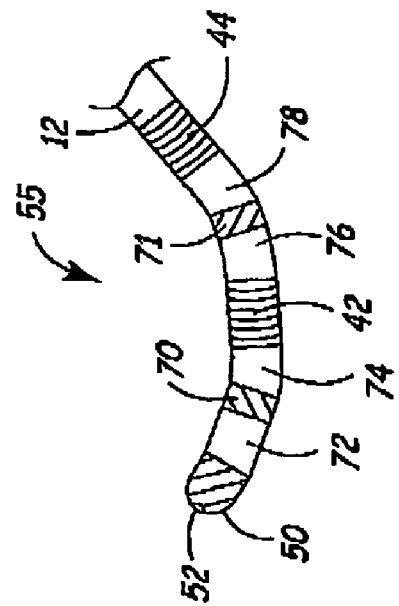
FIG. 10H is a plan view of a distal end of the multilumen body of FIG. 10B illustrating deflection of the distal end at two steering member anchoring points.
Figure 10C:
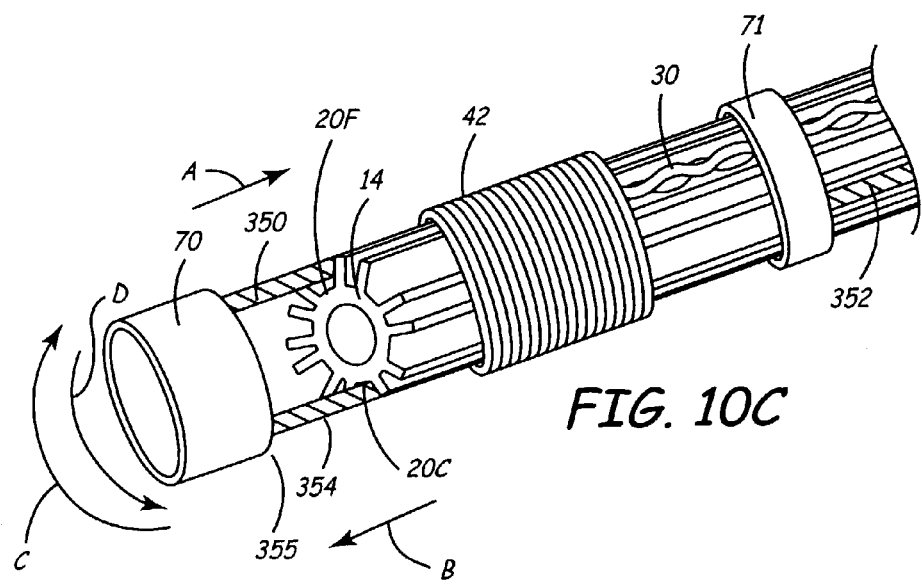
FIG. 10C is a partially exploded, perspective view of the multilumen body of FIG. 10B illustrating the assembly of multiple steering members to different anchoring points.
Figure 10D:
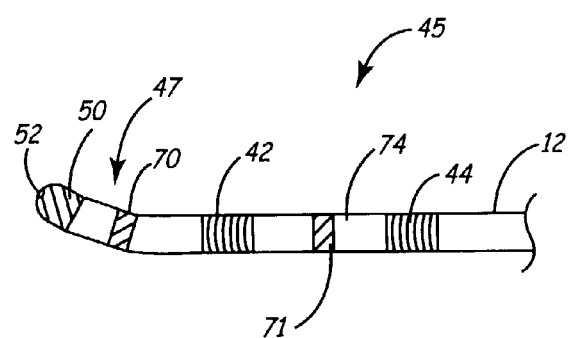
FIG. 10D is a plan view of a distal end of a multilumen body, according to the present invention, in a deflected position.

FIG. 10C is a partially exploded, perspective view of the multilumen body 10 of FIG. 10B illustrating the assembly of multiple steering members to different anchoring points. FIG. 10D is a plan view of a distal end of a multilumen body, according to the present invention, in a deflected position. As illustrated in FIGS. 1A, 1C and 10D, steering member 350 and steering member 354 are fixedly attached, by welding or other appropriate methods, to anchoring member 70. For example, as illustrated in FIG. 10C, steering member 350 is positioned within lumen 20f, while steering member 354 is positioned within lumen 20c so that steering member 350 is positioned approximately 180 degrees about inner insulating member 14 and outer insulating member 12 from steering member 354. In this way, steering members 350 and 354 are diametrically opposed so as to act as an antagonist pair in imposing curvature in two directions or straightening the distal end 45 of multilumen body 10 in a plane defined by steering members 350 and 354. For example, steering member 350 is retracted in a direction shown by arrow A, while steering member 354 is advanced in a direction generally opposite to direction A, shown by arrow B, causing deflection of distal end 45 of body 10 in a direction shown by arrow C so that a curved portion 47 is formed along distal end 45 of multilumen body 10 distal from sensor 42. In order to advance distal end 45 from the deflected position of FIG. 10D to the non-deflected position of FIG. 10B so that body 10 is generally straightened, steering member 354 is subsequently retracted by being advanced in direction A, while steering member 350 is advanced in direction B.

Figure 10E:
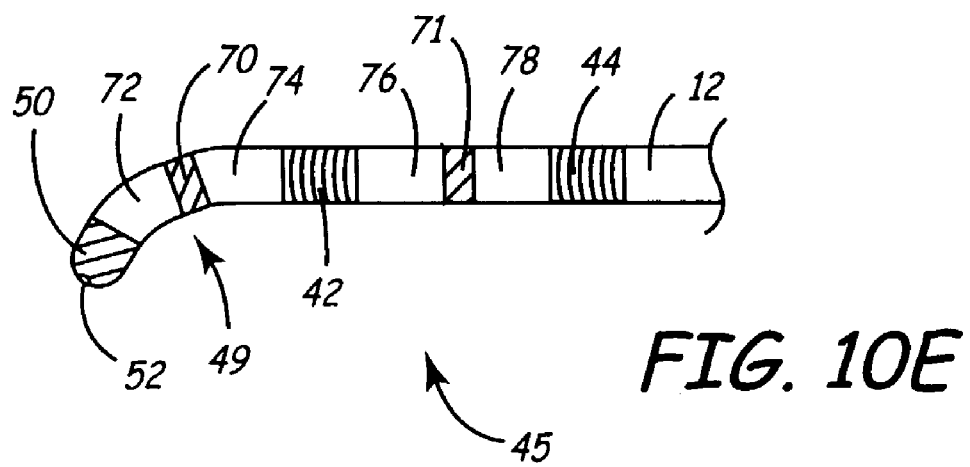
FIG. 10E is a plan view of a distal end of a multilumen body, according to the present invention, in a deflected position.

FIG. 10E is a plan view of a distal end of a multilumen body, according to the present invention, in a deflected position. In the same way, in order to advance distal end 45 from the non-deflected position of FIG. 10B to a deflected position shown in FIG. 10E, steering member 354 is retracted in direction A, while steering member 350 is advanced in direction B, causing deflection of distal end 45 in an opposite direction, shown by arrow D, so that a curved portion 49 is formed along distal end 45 distal from sensor 42.

FIG. 10F is a plan view of a distal end of a multilumen body, according to the present invention, in a deflected position. As illustrated in FIGS. 10A, 10C and 10F, steering member 352 and steering member 356 are fixedly attached, by welding or other appropriate methods, to anchoring member 71. For example, steering member 352 is positioned within lumen 20d, while steering member 356 is positioned within lumen 20a so that steering member 352 is positioned approximately 180 degrees about inner insulating member 14 and outer insulating member 12 from steering member 356. In this way, steering members 352 and 356 are diametrically opposed so as to act as an antagonist pair in imposing curvature in two directions or straightening the distal end 45 of multilumen body 10 in a plane defined by steering members 352 and 356. For example, steering member 356 is retracted in a direction shown by arrow A, while steering member 352 is advanced in direction B, causing deflection of distal end 45 of body 10 in a direction shown by arrow C so that a curved portion 51 is formed along distal end 45 of multilumen body 10 proximal to sensor 42 and distal to sensor 44. In order to advance distal end 45 from the deflected position of FIG. 10F to the non-deflected position of FIG. 10B so that body 10 is generally straightened, steering member 352 is subsequently retracted by being advanced in direction A, while steering member 356 is advanced in direction B.

Figure 10G:
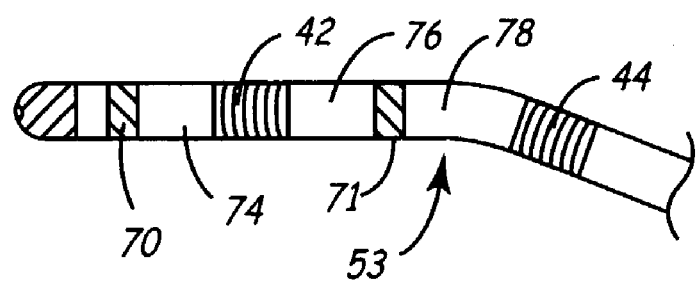
FIG. 10G is a plan view of a distal end of a multilumen body, according to the present invention, in a deflected position.

FIG. 10G is a plan view of a distal end of a multilumen body, according to the present invention, in a deflected position. In the same way, in order to advance distal end 45 from the non-deflected position of FIG. 10B to a deflected position shown in FIG. 10G, steering member 352 is retracted in direction A, while steering member 356 is advanced in direction B, causing deflection of distal end 45 in direction D, so that a curved portion 53 is formed along distal end 45 proximal to sensor 42 and distal to sensor 44. Assembly of inner insulating member 14 with outer insulation segments (not shown), location sensors 42 and 44 and respective conductors 30 and 32 may be performed in the manner generally described above. Outer insulation segments 72 and 74 shown in FIG. 10B may be provided without inward radiating splines and/or may be formed from a lower durometer polymer than the remainder of outer insulating member 12 to enhance the flexibility of the distal end of multilumen body 10.

FIG. 10H is a plan view of the distal end of the multilumen body of FIG. 10B illustrating deflection of the distal end at two steering member anchoring points. As illustrated in FIG. 10H, according to the present invention, distal end 45 of multilumen body 10 is advanced from the non-deflected position to a deflected position illustrated in FIG. 10H by combining the advancement and retraction of steering members 350 and 354 described above in reference to FIG. 10D to form curved portion 47 with the advancement and retraction of steering members 352 and 356 described above in reference to FIG. 10F to form curved portion 51, so that a curved portion 55 is formed distal to sensor 44, for example. In the same way, steering member 352 or 356 fixedly attached to anchoring member 71 is retracted to cause the distal end of body 10 to form a curved portion, such as curved portion 51, for example, in addition to a curve already imposed by steering members 350 and 354 fixedly attached to anchoring member 70, such as curved portion 47, for example, and so forth.

It is understood that the present invention is not intended to be limited to forming the curvatures of the distal end illustrated in FGIS 10D-10H. Rather, the present invention is intended to include use of any number of steering members to form any number of curves or combinations of curves along distal end 45 that may be desired for advancement of multilumen body 10 within a patient.

Alternative embodiments may include any combination of multiple steering members fixedly attached to one or more anchoring members. In addition, it is understood that the present invention is intended to include multiple steering members attached to a single anchoring member that would allow varying degrees of curvature to be imposed in varying directions along different radial planes defined by the center axis of a multilumen body and a given steering member. Steering members may be arranged in antagonistic pairs as described above to allow deflection in two directions along a plane defined by the two steering members. Multiple pairs may be attached to corresponding anchoring members spaced longitudinally along a distal segment of a multilumen body to allow bi-directional deflection to occur at different longitudinal locations. In alternative embodiments, steering members may be attached singly to anchoring members spaced longitudinally along a distal segment of multilumen body 10 allowing curvature to be applied in one direction corresponding to each anchoring point.

Figure 11A:
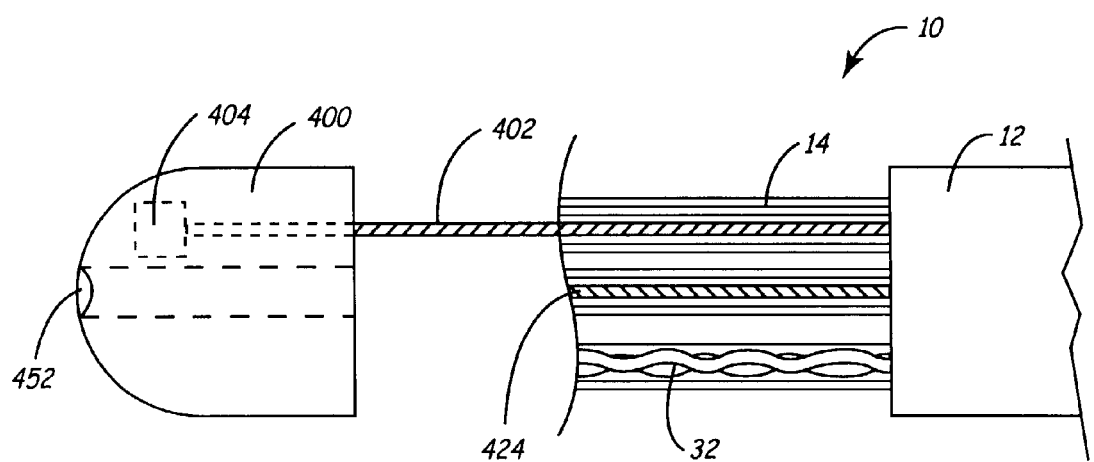
FIG. 11A is a plan view of a steerable, navigable multilumen body including an optional steering sensor and multiple steering members.

FIG. 11A is a plan view of a steerable, navigable multilumen body including an optional steering sensor according to the present invention. As illustrated in FIG. 11A, according to an embodiment of the present invention, a steering sensor 404, which may be an ultrasound, proximity, force, torque or other type of transducer, is included in an end cap member 400 for providing a feedback signal that may be used in guide the steering of multilumen body 10. A steering sensor that may be included in a multilumen body provided by the present invention is generally disclosed in U.S. Pat. No. 6,083,170 issued to Ben-Haim, incorporated herein by reference in its entirety. Steering sensor 404 is coupled to a conductor 402 for carrying signals to a signal processing system. One or more steering sensors may be included in cap member 400 with corresponding conductors extending through isolated individual lumens of multilumen body 10 formed from splined inner and outer insulating members 14 and 12. Other elements may be carried in other lumens of body 10 as required for other components carried by body 10, such as a twisted pair conductor 34 associated with a location sensor (not shown) and a steering member 424 associated with the steering system.

Figure 11B:
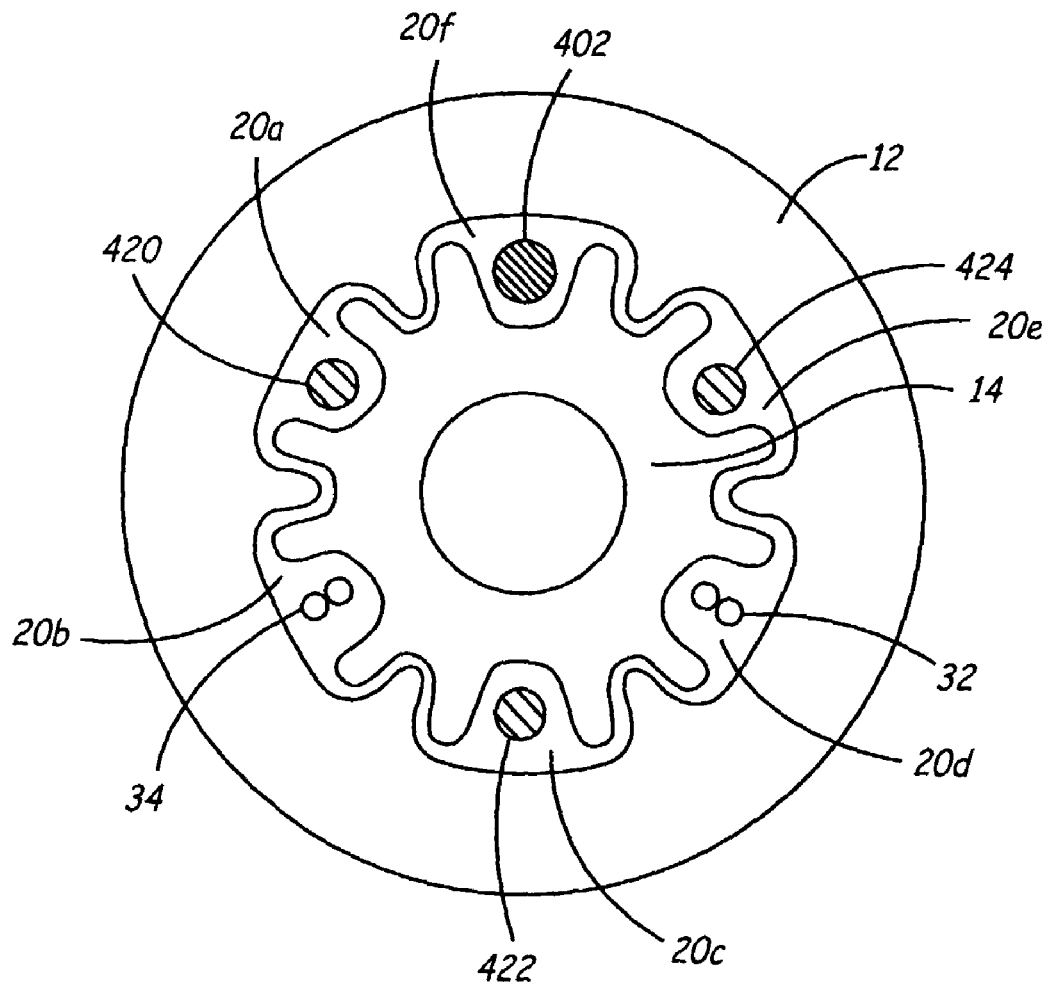
FIG. 11B is a sectional view of the multilumen body of FIG. 11A.

The steering sensor signals indicate information about surrounding tissue or obstructions, such as the density or shape of the tissue, that may be used in determining a direction in which the multilumen body should be deflected or advanced using one or more steering members. FIG. 11B is a sectional view of the multilumen body of FIG. 11A. As illustrated in FIG. 11B, multiple steering members 420, 422, and 424 are carried in multiple lumens 20a, 20c, and 20e in order to more precisely steer the multilumen body along an internal body pathway. The steering members may be activatable shape memory elements as generally disclosed in '170 patent.

Figure 11C:
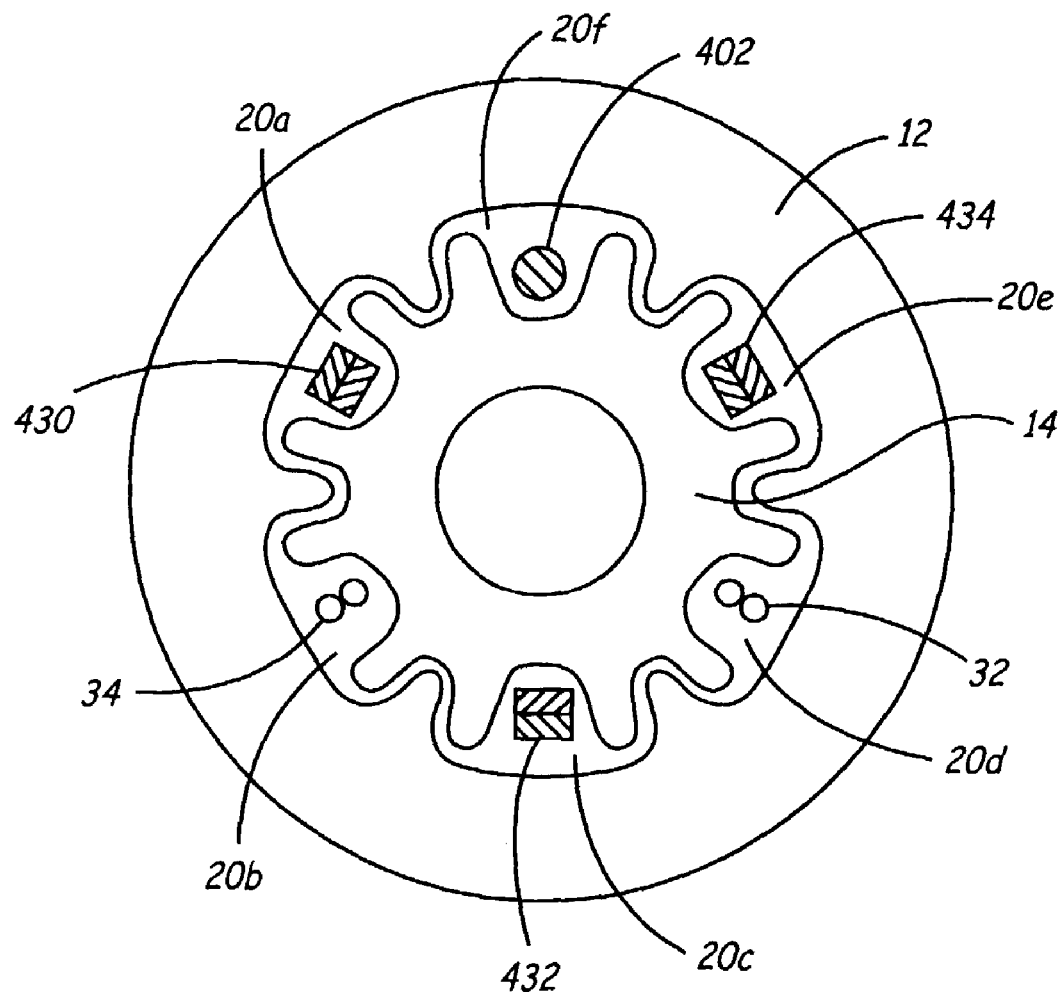
FIG. 11C is a sectional view of an alternative embodiment of the multilumen body of FIG. 11A.

FIG. 11C is a sectional view of an alternate embodiment of the multilumen body of FIG. 11A. As illustrated in FIG. 11C, according to an alternate embodiment of the present invention, multiple steering elements 430, 432, and 434 are provided as bimetal elements which may be bent or straightened in response to temperature changes as generally disclosed in the '170 patent. Multilumen body 10 in this embodiment is provided with generally square-shaped lumens 20a, 20c, and 20e to accommodate bimetal steering elements 430, 432, and 434.

Thus, an improved multilumen body for use in elongated medical devices has been described. Numerous types of elongated medical devices requiring multiple lumens may benefit from the relative advantages of a splined multilumen body provided in accordance with the present invention, which include but are not limited to well-isolated sealed lumens, good torque transfer from a proximal to distal end, good kink-resistance, and a versatile platform for including various combinations of sensors, conductors, medical therapy or diagnostic devices, or open delivery lumens, which may vary in size and shape. Detailed embodiments described above are intended to be exemplary of the concepts of the present invention and should not be considered limiting with regard to the following claims.

What is claimed is:

1. A multilumen body of an implantable medical device extending from a proximal end to a distal end, comprising:
   a first tubular member including an inner wall and at least one member extending inward from the inner wall, the inward extending member further extending longitudinally from the proximal end to the distal end of the multilumen body;
   a second tubular member, positioned within the first member, the second tubular member including an outer wall and at least one pair of members extending outward from the outer wall, the at least one pair further extending longitudinally from the proximal end to the distal end of the multilumen body and forming a groove, the groove receiving the inward extending member of the first tubular member;
   wherein the first tubular member and the second tubular member form at least one lumen extending between the inner wall of the first member and the outer wall of the second member from the proximal end through the distal end of the multilumen body, the at least one lumen receiving an elongated member therein.

2. The multilumen body of claim 1, wherein torque applied along the proximal end of the multilumen body is transferred to the distal end of the multilumen body through the first tubular member and the second tubular member.

3. The multilumen body of claim 1, further comprising an inner lumen formed centrally within the second tubular member for delivering one of a medical device and a therapy.

4. The multilumen body of claim 1, wherein the first tubular member is formed of a first material and the second tubular member is formed of a second material different from the first material.

5. The multilumen body of claim 1, further comprising a sensor located along a length of the multilumen body, wherein the elongated member comprises a conductor coupled to the sensor.

6. The multilumen body of claim 5, wherein the sensor is selected from the group consisting of a location sensor, a steering sensor, an absolute pressure sensor, a temperature sensor, an oxygen sensor, a pH sensor, and an acoustical sensor.

7. The multilumen body of claim 5, wherein the conductor includes a first wire having a first distal segment and a second wire having a second distal segment forming a twisted pair, and the sensor includes a wound conductive wire extending from a first end to a second end, wherein a portion of the first end is helically engaged about the first distal segment and the second end is helically engaged about the second distal segment.

8. The multilumen body of claim 1, further comprising an anchoring member positioned along the distal end of the multilumen body, wherein the elongated member comprises deflection member coupled to the anchoring member, the deflection member transferring tension applied along the proximal end of the multilumen body to advance the distal end of the multilumen body between a nondeflected position and a deflected position.

9. The multilumen body of claim 1, further comprising an electrode located along a length of the multilumen body, wherein the elongated member comprises a conductor coupled to the plurality of electrodes.

10. The multilumen body of claim 1, further comprising:
   a first anchoring member positioned along the distal end of the multilumen body; and
   a second anchoring member positioned proximally from the first anchoring member along the distal end of the multilumen body, wherein the elongated member comprises a first deflection member and a second deflection member coupled to the first anchoring member, and a third deflection member and a fourth deflection member coupled to the second anchoring member, the first deflection member and the second deflection member advancing a first portion of the distal end of the multilumen body between a first portion non-deflected position and a first portion deflected position to form a first curved portion, and the third deflection member and the fourth deflection member advancing a second portion of the distal end of the multilumen body between a second portion non-deflected position and a second portion deflected position to form a second curved portion.

11. The multilumen body of claim 10, wherein the first portion and the second portion form a third curved portion along the distal end of the multilumen body.

12. The multilumen body of claim 1, wherein the elongated member comprises one or more of a conductor, a fluid delivery needle, and a deflection member.

13. The multilumen body of claim 1, wherein:
   the at least one inward extending member of the first tubular member comprises a plurality of inward extending members spaced apart around a circumference of the inner wall; and
   the at least one pair of outward extending members of the second tubular member comprises a plurality of pairs spaced apart about a circumference of the outer wall, each groove of each pair receiving a corresponding inward extending member of the plurality of inward extending members.

14. The multilumen body of claim 13, wherein the at least one lumen comprises a plurality of lumens, each of the plurality of lumens disposed between adjacent pairs of outward extending members.

15. The multilumen body of claim 14, further comprising:
a first anchoring member positioned along the distal end of the multilumen body; and
a second anchoring member positioned proximally from the first anchoring member along the distal end of the multilumen body;
wherein the elongated member of a first lumen of the plurality of lumens comprises a first deflection member and the elongated member of a second lumen of the plurality of lumens comprises a second deflection member, the first and second deflection members coupled to the first anchoring member to advance a first portion of the distal end of the multilumen body between a first portion non-deflected position and a first portion deflected position to form a first curved portion;
the elongated member of a third lumen of the plurality of lumens comprises a third deflection member and the elongate member of a fourth lumen of the plurality of lumens comprises a fourth deflection member, the third and fourth deflection members coupled to the second anchoring member to advance a second portion of the distal end of the multilumen body between a second portion non-deflected position and a second portion deflected position to form a second curved portion;
the first lumen of the plurality of lumens is positioned approximately 180 degrees from the second lumen of the plurality of lumens about the first and second tubular members; and
the third lumen of the plurality of lumens is positioned approximately 180 degrees from the fourth lumen of the plurality of lumens about the first and second tubular members.

16. The multilumen body of claim 14, wherein the first tubular member further includes an end cap terminating the distal end of the multilumen body and a plurality of guide lumens, each guide lumen of the plurality of guide lumens extending from a corresponding lumen of the plurality of lumens outward through the end cap, and each guide lumen allowing passage of the corresponding elongated member therethrough.

17. The multilumen body of claim 16, wherein the corresponding elongated members comprise fluid delivery needles.

18. The multilumen body of claim 1, wherein the first tubular member further includes an end cap terminating the distal end of the multilumen body and at least one guide lumen extending from the at least one lumen outward through the end cap, the guide lumen allowing passage of the elongated member therethrough.

19. The multilumen body of claim 18, wherein the elongated member comprises a fluid delivery needle.

* * * * *